(12) United States Patent
Kuo

(10) Patent No.: US 7,078,063 B2
(45) Date of Patent: Jul. 18, 2006

(54) **WATER SOLUBLE EXTRACT FROM PLANT OF *SOLANUM* GENUS AND THE PREPARATION PROCESS THEREOF, AND PHARMACEUTICAL COMPOSITION CONTAINING THE WATER SOLUBLE EXTRACT**

(75) Inventor: Kou-Wha Kuo, Kaohsiung (TW)

(73) Assignee: G & E Herbal Biotechnology Co., LTD., Tainan (TW)

( * ) Notice: Subject to any disclaimer, the term of this patent is extended or adjusted under 35 U.S.C. 154(b) by 228 days.

(21) Appl. No.: 10/650,942

(22) Filed: Aug. 29, 2003

(65) Prior Publication Data
US 2004/0247715 A1 Dec. 9, 2004

(30) Foreign Application Priority Data
Jun. 5, 2003 (TW) .................................. 92115249

(51) Int. Cl.
*A61K 35/78* (2006.01)
(52) U.S. Cl. ...................... 424/725; 424/773; 424/774; 424/777; 424/779
(58) Field of Classification Search .................... None
See application file for complete search history.

(56) References Cited

U.S. PATENT DOCUMENTS

| | | | |
|---|---|---|---|
| 3,960,839 A | 6/1976 | Guerrero | |
| 5,958,770 A | 9/1999 | Cham et al. | |
| 6,149,912 A | 11/2000 | Gubarev et al. | |
| 6,180,154 B1 | 1/2001 | Wrolstad et al. | |
| 6,214,803 B1 | 4/2001 | Kuo et al. | |
| 2004/0249138 A1 * | 12/2004 | Lawson | |

FOREIGN PATENT DOCUMENTS

| | | |
|---|---|---|
| EP | 0 020 029 | 12/1980 |
| NZ | 529466 | 3/2004 |
| WO | WO 00/61153 | 10/2000 |
| WO | WO 03/029269 A1 | 4/2003 |

OTHER PUBLICATIONS

Lin et al.; "Novel Antihepatotoxic Principles of *Solanum* ", Planta medica 1988 p. 222.
Gan et al. "Cytotoxic Principles and Their Derivatives of Formosan *Solanum* Plants", Journal of Natural Products, vol. 56, No. 1, pp. 15-21, Jan. 1993.
Chang et al. "The Rhamnose Molety of Solamargine Plays a Crucial Role in Triggering Cell Death by Apoptosis", Biochemical and Biophysical Research Communications 242, pp. 21-25 (1998) Article No. RC977903.
Lin et al. "The Cytotoxic Principles of *Solanum Incanum* ", Journal of Natural Products, 53(2), 513-516 (1990).
Hsu et al. "Solamargine Purified from *Solanum incanum* Chinese Herb Triggers Gene Expression of Human TNFR 1 Which May Lead to Cell Apoptosis", Biochemical and Biophysical Research Communications 229, 1-5 (1996) article no. 1748.
http://fsweb.berry.edu/Academic/MANS/mcipollini/bio313w/files/ecobioch.htm, Dec. 27, 2003.
TW 471968 (Jan. 11,2002) *Abstract.
CN 1 345 728 (Apr. 24, 2002). *Abstract.
Abstract Number IC0563 from the 20th World Congress of Dermatology Skin carcinoma (part I) Interactive, Jul. 2, 2002, "A Double Blind, randomized, parallel group, vehicle-controlled multicentric study of solasodine glycoside cream in basel cell carcinoma (BCC)" *Abstract.
http://www.genesisny.net/Medical/RXmedBreakthrough.html, -Dec. 27, 2003.
European Search Report of EP 03 25 5206.
Katsuya Fukuhara et al., "Isolation of the Steroidal Glycoalkaloids from *Solanum incanum* by two Countercurrent Chromatographic Methods", Phytochemistry, vol. 30, No. 2, pp. 685-687 (1991).
Kou-Wha Kuo et al., "Anticancer Activity Evaluation of the *Solanum* Glycoalkaloid Solamargine", Biochemical Pharmacology, vol. 60, pp. 1865-1873, 2000.
Ke Hu et al., "Antineoplastic Agents III: Steroidal Glycosides from *Solanum nigrum* ", Planta Medica 65 (1999) pp. 35-38.
Chang et al., "Experimental Antitumor Agents from *Solanum indicum* L", Cancer Research, 11: 1911-1918 (1991).

* cited by examiner

Primary Examiner—Susan D. Coe
(74) Attorney, Agent, or Firm—Foley & Lardner LLP

(57) ABSTRACT

A water soluble extract from a plant of *Solanum* genus consists essentially of at least 60%–90% of solamargine and solasonine. A process for preparing the water soluble extract from the plant of *Solanum* genus involves the steps of hydrolysis with an acid, precipitation with a base, and separation treatments using chloroform, alcohol and water as extraction solvents. The water soluble extract prepared from the process can be directly dissolved in pure or neutral pH water to form a yellowish clear and transparent aqueous solution having a water solubility ranging from 2~20 mg/ml or higher.

The water soluble extract can be used as an active component in a pharmaceutical composition for inhibiting the growth of tumor/cancer cells, in particular liver cancer cells, lung cancer cells and breast cancer cells.

59 Claims, 21 Drawing Sheets

WATER SOLUBLE EXTRACT FROM PLANT OF *SOLANUM* GENUS AND THE PREPARATION PROCESS THEREOF, AND PHARMACEUTICAL COMPOSITION CONTAINING THE WATER SOLUBLE EXTRACT

BACKGROUND OF THE INVENTION

1) Field of the Invention

This invention relates to water-soluble extracts from a plant of *Solanum* genus, the preparation processes thereof, and pharmaceutical compositions comprising the same.

2) Description of the Related Art

Cancer is one of the major causes of human death globally, and lung cancer, liver cancer, and breast cancer are most common. Although the mechanism of cancer development has yet to be fully understood, it is believed that the onset of cancer in a subject may be caused by abnormal and uncontrollable cell division occurring in said subject (Chen, P. L., et al. (1990), *Science,* 250, 1576–1580; Finlay, C. A., et al. (1989), *Cell,* 57, 1083–1093, and Baker, S. J., et al. (1990) *Science,* 249, 912–915).

Usually, the growth and differentiation of cells in a human or animal body are strictly controlled by growth hormones present in the human or animal body. When cells accumulate therein gene mutations caused by intrinsic and/or extrinsic factors, said cells will generate incorrect signal transmissions, which in turn lead to the uncontrollable growth and division of cells, thereby resulting in the formation of cancer cells gradually (Kerr, J. F. R. (1971) *J. Pathol.,* 105, 13–20).

In recent years, investigators around the world have endeavored to research works of cancers. However, the currently developed and employed cancer therapies fail to provide satisfactory therapeutic effects. In addition to patients' personal factors, the serious side effects of anti-cancer drugs and the resistance of cancer cells to such drugs are the primary problems encountered in clinical therapy.

In view of the fact that the known western medicines employed in clinic fail to effectively improve the current therapies for cancer dieases, some researchers have, based on the investigation results of the onset mechanism of cancer disease, attempted to find active ingredients from traditional Chinese medicines (TCM) or herbs that can be used to cure or relieve the symptoms of cancers.

Apoptosis is considered to be a natural mechanism that regulates animal cell growth (Martin, S. J. and Green, D. R. (1995), *Crit. Rev. Oncol. Hemat.,* 18, 137–153), and it plays an important role in regulating natural cell death, such as the natural tissue shrinkage and absorption occurring during the growth process of animals. In addition, when human cells are damaged and cannot be repaired, apoptosis will be initiated so as to avoid the formation of cancer cells.

The major morphological features of apoptosis include: formation of apoptotic bodies, chromatin condensation, and DNA fragmentation (Arends, M. J. and Wyllie, A. H. (1991) *Int. Rev. Exp. Pathol.,* 32, 223–254; Dive, C., et al., (1992) *Biochim. Biophys. Acta* 1133, 275–285; and Darzynkiewicz, Z., et al. (1992) *Cytometry,* 13, 795–808). During apoptosis, debris of dead cells will be rapidly ingested by neighboring cells and macrophages via phagocytosis without inducing an inflammatory response (Sarraf, F. E. and Bowen, I. D. (1988) *Cell Tissue Res.* 21, 45–49). In addition, when the variation of cell cycle is detected by flow cytometry, the presence of a sub-G1 peak can be observed (Alzerreca, A. and Hart, G. (1982) *Toxicology Lett.* 12, 151–155; and Lin, C. N., et al. (1986) *J. Taiwan Pharm. Assoc.* 38, 166). Thus, the sub-G1 peak is considered to be a typical marker for identifying cells that are undergoing apoptosis.

It is reported in literature that cells will become cancer cells if the apoptotic mechanism thereof is out of control (Carson, D. A. and Ribeiro, J. M. (1993) *Lancet* 341, 1251–1254; and Kaufmann, S. H. (1989) *Cancer Res.* 49, 5870–5878). Therefore, apoptosis has become a subject of study in oncology. In addition, it is reported that apoptosis can be induced by certain anti-cancer drugs (Wyllie, A. H., et al., (1980) *Int. Rev. Cytol.* 68, 251–306; Wyllie, A. H., et al., (1984) *J Pathol.* 142, 67–77; Barry, M. A., et al. (1990) *Biochem. Pharmacol.,* 40, 2353–2362; and Hickman, J. A. (1992) *Cancer Metast. Rev.,* 11, 121–139). Thus, apoptosis points to a major direction in the global development of anti-cancer drugs.

Use of traditional Chinese medicines or herbal medicines to treat diseases has a long history. At present, not a few researchers are trying to find useful anti-cancer drugs from traditional Chinese medicines or herbal medicines. However, the application of traditional Chinese medicines or herbal medicines is still based on empiricism, and is not supported by sufficient scientific evidence. In addition, because the extraction of active ingredients, and the dosage and quality control of traditional Chinese medicines or herbal medicines are not scientized, the therapeutic effects exhibited by the medicines are not consistent.

Furthermore, most of the active ingredients from traditional Chinese medicines or herbal medicines are water insoluble. When water-insoluble material is orally administered to or injected into animal bodies, the intended therapeutic effect thereof may not be achieved due to difficulty in absorption. These are the major restraints that hamper the development and application of traditional Chinese medicines and herbal medicines.

Plants that can be used as medicines are numerous. It is well known that many protein inhibitors extracted from plant materials are used in anti-cancer therapy. Among these protein inhibitors with anti-cancer potential, steroidal alkaloids from a plant of *Solanum* genus are found to be a potential anti-cancer drug.

It is known that *Solanum incanum* L. (also known as *Solanum incanum* Ruiz. & Pav., *Solanum coagulans* Forsskal in Latin, and bitter apple in English) contains steroidal glycoalkaloid (Kuo, K. W., et al. (2000), *Biochemical Pharmacology,* 60 (12): 1865–73). In addition, many plants of the *Solanum* genus are reported to contain steroidal glycoalkaloid, including, for example, *Solanum indicum, Solanum nigrum,* also known as Long Kui in Chinese and black nightshade in English (Hu, K., et al. (1999), *Planta Medica,* 65 (1): 35–8), *Solanum capsicastrum* (known as false Jerusalem cherry in English), *Solanum xanthocarpum, Solanum melongena* (Blankemeyer, J. T., et al. (1998), *Food &Chemical Toxicology,* 36 (5): 383–9), *Solanum coagulans, Solanum tuberosum* (Friedman, M., et al. (1996), *Journal of Nutrition,* 126 (4): 989–99), *Solanum sodomeum* (known in Australia as apple of Sodom), *Solanum turburosum, Solanum aculeastrum* (Wanyonyi, A. W., et al. (2002), *Phytochemistry,* 59 (1): 79–84), *Solanum lycocarpum* (Peters, V. M., et al. (2001), *Contraception,* 63 (1):53–5), *Solanum khasianum* (Putalun, W., et al. (2000), *Biological &Pharmaceutical Bulletin,* 23 (1): 72–5), *Solanum suaveolens* (Ripperger, H., et al. (1997), *Phytochemistry,* 46 (7): 1279–82), *Solanum uporo* (Ripperger, H., et al. (1997), *Phytochemistry,* 44, (4): 731–4), *Solanum abutiloides* (Tian, R. H., et al. (1997), *Phytochemistry,* 44 (4): 723–6), *Solanum coccineum* (Lorey, S., et al. (1996), *Phytochemistry,* 41 (6): 1633–5), *Solanum unguiculatum* (Sarg, T. M., et al. (1995),

*Pharmacy World &Science*, 17 (6): 191–4), *Solanum robustum* (Ripperger, H. (1995), *Phytochemistry* 39 (6): 1475–7), *Solanum anguivi* (Ripperger, H., et al. (1994), *Phytochemistry*, 37 (6): 1725–7), *Solanum platanifolium* (Puri, R., et al. (1994), *Journal of Natural Products* 57 (5): 587–96), *Solanum mammosum* (Alzerreca, A., et al. (1982), *Toxicology Letters*, 12 (2–3): 151–5), etc.

Up to the present, steroidal alkaloids which can be obtained from the aforesaid plants of *Solanum* genus comprise, for example, solamargine, solasonine, khasianine and solasodine (Chataing, B., et al. (1998), *Planta Medica* 64, 31–36, and Weissenberg, M., et al. (1998), *Phytochemistry* 47, 203–209). The structures of solasonine and solamargine are as follows:

and human PLC/PRF/5 hepatoma cells (Lin, C. N. et al. (1986), *J. Natural Prod.*, 53, 513–516).

Shu-Hui Hsu et al. studied the mechanism of cytotoxicity of solamargine, and found that solamargine increases death of cells, such as Hep3B and normal skin fibroblast cells, by apoptosis pathway. Particularly, it was found that the gene expression of TNF receptor I involved in the process of cell apoptosis was up-regulated by solamargine (Hsu, S. H. et al. (1996), *Biochem. Biophys. Res. Comm.*, 229, 1–5).

Katsuya Fukuhara and Isao Kubohas reported in *Phytochemistry*, 30 (2): 685–687, 1991, that ripe fruits of *Solanum incanum* were extracted with methanol at room temperature. Then, the solvent was removed under reduced pressure, and the residue was lyophilized to give a dark

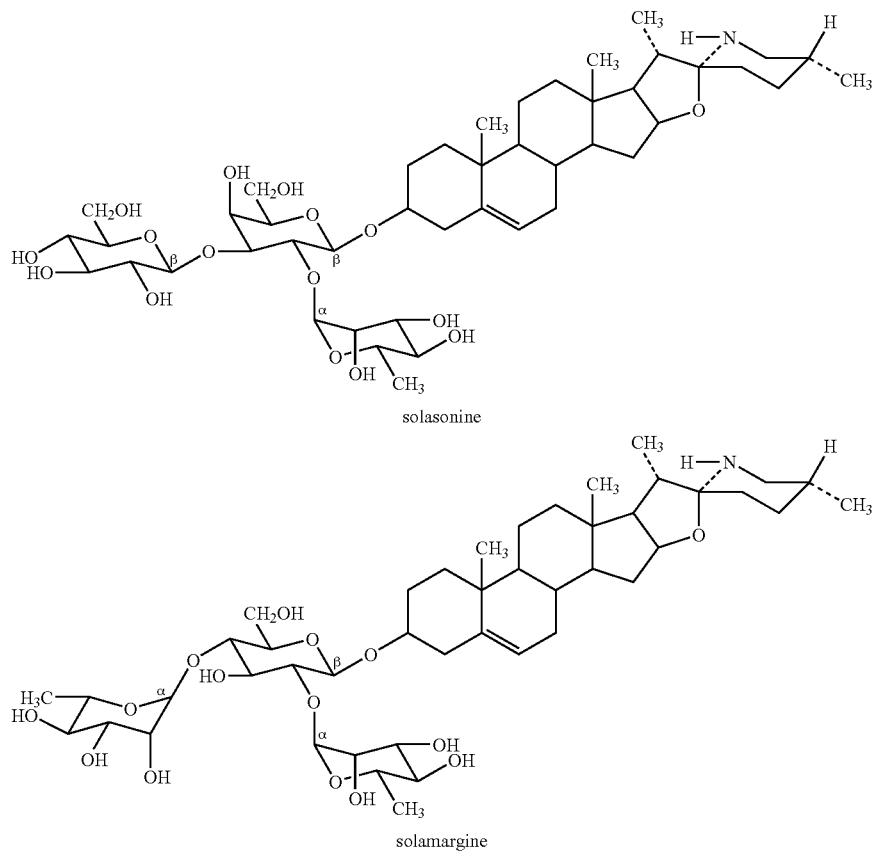

solasonine solamargine

In addition, studies have shown that solamargine obtained from various plant materials is capable of inhibiting growth of the following organisms: parasites, such as *Trypanosoma cruzi*; insects, such as *Tribolium castaneum* (known as red flour beetle), *Manduca sexta* (known as tobacco hornworm); mold, such as *Phoma medicaginis* and *Rhizoctomia solani*; and mollusks, such as *Lymnaea cubensis* and *Biomphalaria glabrata* (Chataing, B., et al. (1998), *Planta Medica*, 64, 31–36; Fewell, A. M., et al. (1994), *Phytochemistry*, 37, 1007–1011; Lin, C. N., et al. (1990), *J. Nat. Prod.*, 53, 513–516).

Furthermore, Chun-Nan Lin et al. reported that solamargine can be obtained from the fruit of *Solanum incanum*, and the structure thereof belongs to steroidal alkaloid glycoside. It is found that the compound protects the liver from $CCl_4$-induced damage, and inhibits the growth of JTC-26 brown extract. Next, the extract was suspended in water containing methanol (1%). After removing the water insoluble portion, the suspension was partitioned with n-hexane, chloroform, ethyl acetate, and water, and an aqueous layer with bioactivity was obtained. The aqueous layer with bioactivity thus obtained was subsequently subjected to rotation locular countercurrent chromatography and droplet countercurrent chromatography such that solamargine and solasonine, the two major compounds, were obtained.

It was disclosed by Ke Hu et al. (1999) in *Planta Medica* 65, 35–38, that a dried whole herb of *Solanum nigrum* was refluxed with 75% EtOH. The solvent was removed in vacuo to obtain a brown residue, which was defatted with petroleum ether to give an extract. The resultant extract was suspended in water and was subjected to chromatography on a macroresin column. There is an active compound present in 60% EtOH eluent. 60% EtOH eluent was then partitioned with H$_2$O and extracted with n-BuOH, and the n-BuOH extract thus obtained was subjected to column chromatography on silica gel using CHCl$_3$—MeOH—H$_2$O as an eluant and on Sephadex LH-20 using MeOH—H$_2$O (60:40) as an eluant, yielding β$_2$-solamargine, solamargine and degalactotigonin. However, this paper did not teach how a water-soluble bioactive extract can be obtained from *Solanum nigrum*.

EP 0 020 029 A1 disclosed that a plant material of *Solanum sodomeum*, known in Australia as apple of Sodom, was extracted with a diluted acid solution, such as 2% or 3% acetic acid, to obtain a first acidic extract (supernatant portion), and the solid residue was then extracted with another volume of the diluted acid solution after being separated from the first acidic extract so as to yield a second acidic extract (supernatant portion). After combining the first and second acidic extracts, a base was added to obtain a precipitate. The precipitate was dissolved in boiling ethanol. After removal of ethanol, a fine powder extract (referred to as BEC 001) was obtained. BEC 001 extract was further separated and purified to yield various glycoalkaloids, including solamargine, solasonine, and mono- and di-glycosides of soladodine.

Although EP 0 020 029 A1 mentioned that H$_2$O can be used as a carrier for BEC 001 extract, the extract was essentially formulated with dimethyl sulfoxide solution (DMSO), paraffin, zinc ointment, zinc cream, and cetomacrogol (a surfactant) in the working examples of said patent.

Furthermore, according to U.S. Pat. No. 5,958,770, solasodine glycosides used in the cytotoxic experiment in vitro were first dissolved in DMSO and then diluted to give a 5% DMSO solution. In addition, solasodine glycosides employed in the experiment were either in a form of a mixture (referred to as BEC) including solamargine (33%), solasonine (33%), and di- and mono-glycoside (34%), or in a form of a separate component (solamargine, solasonine, a mixture of di- and mono-glycoside, and the aglycones of solasodine).

Since the aforesaid steroidal alkaloids are water-insoluble, alcohol distillation is a common extracting method used in the aforesaid patents or literatures, and the extracted portions are usually dissolved in an organic solvent, i.e. DMSO for analysis. Because water-insoluble materials are not suitable for direct injection into animal bodies and may not be absorbable by the digestive tract during oral administration, the therapeutic effects of steroidal alkaloids cannot be achieved, thereby limiting the pharmaceutical application and development of steroidal alkaloids.

The applicant found that the dried powders of solamargine and/or solasonine definitely could not dissolve in water without being pre-treated with DMSO, and may not completely dissolve in water even after being treated with DMSO. Specifically, steroidal alkaloids extracted by using the method disclosed in EP 0 020 029 A1 could not dissolve in distilled water. Although solamargine or solasonine can dissolve in water after being first dissolved in DMSO, they will be precipitated if the concentration thereof is too high (more than 5 mg/ml). In addition, DMSO (>1%) per se has a strong cytotoxicity to cells, and thus, the concentration thereof should be controlled to be less than 5%. Such facts clearly indicate that the use of DMSO organic solvent to dissolve steroidal alkaloids extracted from a plant of *Solanum* genus has limitations.

In view of the foregoing, at present, steroidal alkaloids are primarily produced by chemical manufacturers on a limited and small scale basis and in single batches, and there is not an efficient process for extracting water-soluble steroidal alkaloids from a plant of *Solanum* genus on a large scale for commercial use. As such, the application of steroidal alkaloids in the manufacture of medicaments and drugs is limited.

SUMMARY OF THE INVENTION

Accordingly, in the first aspect, in order to produce water-soluble steroidal alkaloids from a plant of *Solanum* genus on a large scale, this invention provides a water-soluble extract from a plant of *Solanum* genus, wherein the extract consists essentially of at least 60%–90% of solamargine and solasonine and can be directly dissolved in pure water or water with a neutral pH value without addition of any other solvent and/or solvent adjuvant, such that a yellowish clear and transparent aqueous solution having a water solubility ranging from 2 to 20 mg/ml or higher is formed.

In the second aspect, this invention provides a pharmaceutical composition comprising the water-soluble extract as an active ingredient for inhibiting the growth of tumor/cancer cells, especially liver cancer cells, lung cancer cells, and breast cancer cells.

In the third aspect, this invention provides a process for preparing a water-soluble extract from a plant of *Solanum* genus, comprising the steps of:

(a) subjecting a plant material of a plant of *Solanum* genus to an extraction treatment using an acidic aqueous solution with a pH value of 3~5, such that an aqueous solution is obtained;

(b) adjusting the pH value of the aqueous solution obtained in step (a) to pH 8~10 with a base, such that a precipitate is formed;

(c) washing the precipitate formed in step (b) with water, followed by drying, such that a dried product is obtained;

(d) admixing the dried product obtained in step (c) with chloroform, followed by addition of a suitable amount of a 100% alcohol, such that a chloroform-alcohol mixture is formed;

(e) mixing the chloroform-alcohol mixture formed in step (d) with a water/alcohol solution having a predetermined water:alcohol ratio, such that a mixture containing a chloroform-based layer and a non-chloroform-based layer is obtained;

(f) removing the chloroform-based layer from the mixture obtained in step (e), followed by addition of a suitable amount of water; and (g) obtaining a supernatant from the resultant mixture of step (f), followed by drying the supernatant, wherein the resultant dried product is able to be directly dissolved in water to form a yellowish clear and transparent aqueous solution.

BRIEF DESCRIPTION OF THE DRAWINGS

The above and other objects, features, and advantages of the present invention will become apparent with reference to the following detailed description and the preferred embodiments taken in conjunction with the accompanying drawings, in which.

DETAILED DESCRIPTION OF THE INVENTION

Figure 1A:
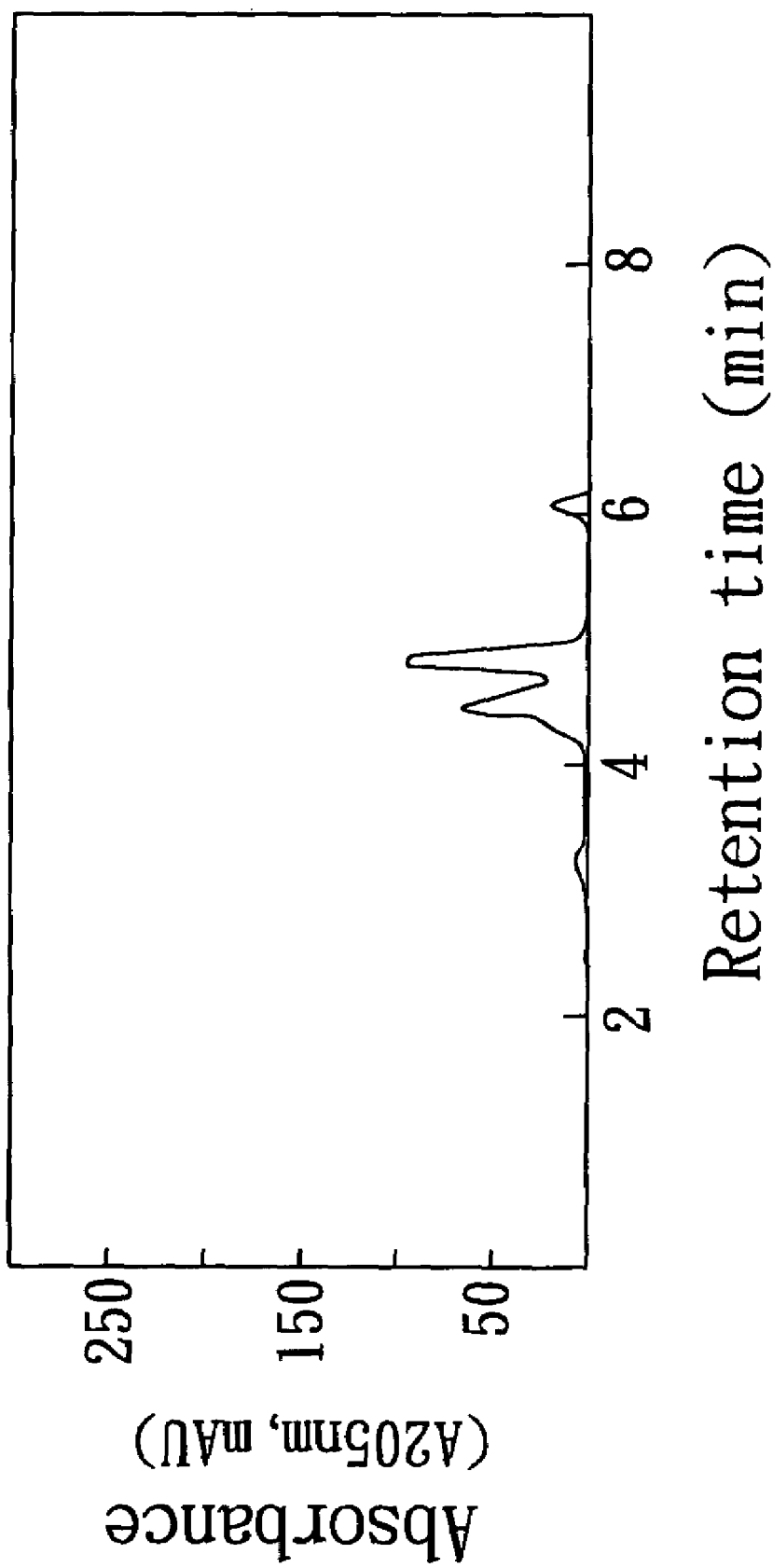
FIG. 1A shows HPLC spectrum of the water-soluble extract (25 μg) obtained from *Solanum incanum* L.
Figure 1:
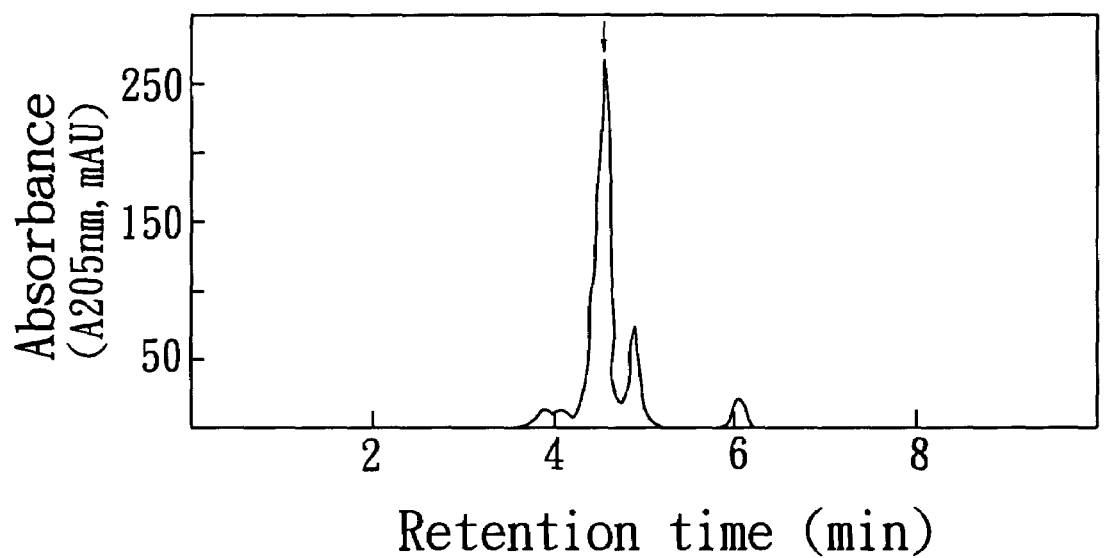
FIG. 1B shows HPLC spectrum of the water-soluble extract (25 μg) obtained from *Solanum incanum* L. in combination with solasonine (5 μg)
FIG. 1C shows HPLC spectrum of the water-soluble extract (25 μg) obtained from *Solanum incanum* L. in combination with solamargine (51μg)
Figure 1:
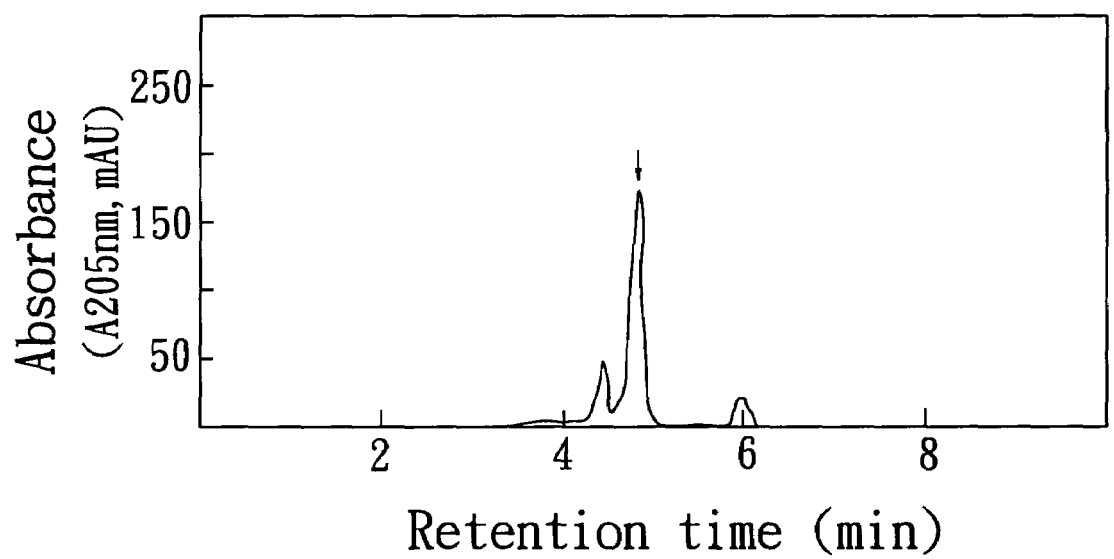

This invention provides a water-soluble extract obtained from a plant of *Solanum* genus comprising steroidal alkaloids which can directly dissolve in water to form a clear and transparent aqueous solution, and thus is suitable for the manufacture of medicaments and drugs.

In particular, this invention provides a water-soluble extract obtained from a plant of *Solanum* genus, which consists essentially of at least 60%–90% of solamargine and solasonine, and can be directly dissolved in pure water or water with a neutral pH value without adding any other solvent and/or solvent adjuvant, such that a yellowish clear and transparent aqueous solution having a water solubility ranging from 2 to 20 mg/ml or higher is formed.

This invention provides a process for preparing a water-soluble extract, which comprises the steps of:

(a) subjecting a plant material of a plant of *Solanum* genus to an extraction treatment using an acidic aqueous solution with a pH value of 3~5, such that an aqueous solution is obtained;

(b) adjusting the pH value of the aqueous solution obtained in step (a) to pH 8~10 with a base, such that a precipitate is formed;

(c) washing the precipitate formed in step (b) with water, followed by drying, such that a dried product is obtained;

(d) admixing the dried product obtained in step (c) with chloroform, followed by addition of a suitable amount of a 100% alcohol, such that a chloroform-alcohol mixture is formed;

(e) mixing the chloroform-alcohol mixture formed in step (d) with a water/alcohol solution having a predetermined water:alcohol ratio, such that a mixture containing a chloroform-based layer and a non-chloroform-based layer is obtained;

(f) removing the chloroform-based layer from the mixture obtained in step (e), followed by addition of a suitable amount of water; and (g) obtaining a supernatant from the resultant mixture of step (f), followed by drying the supernatant, wherein the resultant dried product is able to be directly dissolved in water to form a yellowish clear and transparent aqueous solution.

Preferably, in step (a), the plant material of the plant of *Solanum* genus has been chopped in a preliminary treatment.

Preferably, in step (a), the plant material is at least one of the fruit, root, stem, and leaf of the plant of *Solanum* genus. In a preferred embodiment of this invention, the plant material used in step (a) is the fruit of the plant of *Solanum* genus. In a further preferred embodiment of this invention, the plant material used in step (a) is the whole plant of the plant of *Solanum* genus.

Preferably, the water-soluble extract is obtained from a plant of *Solanum* genus selected from the group consisting of *Solanum incanum* L., *Solanum indicum, Solanum nigrum, Solanum capsicastrum, Solanum xanthocarpum, Solanum melongena, Solanum coagulans, Solanum tunigrum, Solanum sodomeum, Solanum turburosum, Solanum aculeastrum, Solanum lycocarpum, Solanum khasianum, Solanum suaveolens, Solanum uporo, Solanum abutiloides, Solanum coccineum, Solanum unguiculatum, Solanum robustum, Solanum anguivi, Solanum platanifolium,* and *Solanum mammosum.*

In a preferred embodiment of this invention, the water-soluble extract is obtained from *Solanum incanum* L. In a further preferred embodiment of this invention, the water-soluble extract is obtained form *Solanum nigrum*.

Preferably, in step (a) of the process, the aqueous solution is obtained by conducting centrifugation or filtration subsequent to the extraction treatment.

Preferably, in step (a), the acidic aqueous solution used in the extraction treatment is an aqueous solution containing formic acid, acetic acid, or hydrochloric acid.

Preferably, in step (b), the base is preferably an alkaline aqueous solution containing a compound selected from the group consisting of alkali hydroxides and ammonium hydroxide. In a preferred embodiment of this invention, the alkaline aqueous solution contains ammonium hydroxide. In another preferred embodiment of this invention, the alkaline aqueous solution contains sodium hydroxide.

Preferably, in step (b) of the process, the precipitate is obtained by conducting centrifugation or filtration subsequent to the pH value adjustment.

Preferably, in step (c) of the process, the drying treatment is selected from the group consisting of lyophilization, spray-drying, evaporation, heat-drying, and a combination thereof. In one preferred embodiment of this invention, the drying treatment is performed by lyophilization, which is used to improve the stability and activity of the active ingredient by low temperature treatment.

Preferably, in step (c) of the process, the precipitate formed in step (b) is washed with water, centrifuged to remove the excess base, and suspended in distilled water, followed by the drying treatment.

In step (d) of the process, the amounts of chloroform and alcohol are not particularly critical, as long as the dried product obtained from step (c) can dissolve therein. In a preferred embodiment of this invention, the amount of alcohol is not greater than that of the chloroform used in step (d).

Preferably, in steps (d) and (e) of the process, the alcohol is selected from the group consisting of methanol, ethanol, propyl alcohol, and a combination thereof. In a preferred embodiment of the present invention, the alcohol used in steps (d) and (e) is methanol.

Preferably, in the water/alcohol solution used in step (e), the water content is not less than the alcohol content. More preferably, the water to alcohol ratio is 1:1.

Preferably, in step (f) of the process, the chloroform-based layer in the mixture obtained from step (e) is removed by conducting centrifugation or filtration.

Preferably, in step (g) of the process, the supernatant is obtained by centrifuging or filtering the resultant mixture in step (f).

Preferably, in step (g) of the process, the drying treatment is selected from the group consisting of lyophilization, spray-drying, evaporation, concentration under reduced pressure, heat-drying, and a combination thereof. In a preferred embodiment, the drying treatment performed in step (g) comprises concentration under reduced pressure and lyophilization.

If desired, the dried product obtained in step (g) can be re-dissolved in water, followed by centrifugation and drying treatment.

The extract according to this invention can directly dissolve in drinking water or sterile water so as to form a yellowish clear and transparent solution. Accordingly, the extract obtained according to this invention is truly a water-soluble extract.

The water-soluble extract prepared from the present process consists essentially of at least 60%–90% of solamargine and solasonine. In addition, the applicant found that certain factors might affect the content and proportion of solasonine and solamargine in the water-soluble extract obtained using the process of this invention. These factors include the species of the plant of *Solanum* genus and the part/parts of the plant used in the extracting process, as well as the types of alcohol and base used.

For example, in the water-soluble extract produced from the ripe fruit of *Solanum incanum* L., the content of solamargine is higher than that of solasonine according to HPLC analysis. Furthermore, compared with 33% basic $NH_4OH$ solution, in the water-soluble extract obtained by using 10M NaOH basic solution as the base in step (b), the solamargine content is less than the solasonine content. In addition, the contents of solasonine and solamargine in the water-soluble extract obtained by using ethanol in step (d) are about 50% of that obtained by using methanol. In addition, the extract obtained from the unripe fruit (dark green color) of *Solanum nigrum* has higher contents of solasonine and solamargine, whereas the ripe fruit (dark purple color) and other parts of the plant have lower contents. The contents of solasonine and solamargine in the extract from *Solanum nigrum* are different from those in the extract obtained from *Solanum incanum* L. Therefore, a skilled artisan can prepare a desired water-soluble extract by selecting a suitable species of the plant of *Solanum* genus and using a suitable part or parts of the plant, in conjunction with appropriate operating conditions.

In a preferred embodiment of this invention, the aqueous solution used in step (a) to perform extraction treatment contains acetic acid, the basic solution used in step (b) to form the precipitate contains ammonium hydroxide, and the alcohol used in steps (d) and (e) is methanol.

Preferably, the water-soluble extract is composed of more than 75% of solamargine and solasonine.

The solasonine to solamargine ratio in the water-soluble extract is preferably in a range of from 0.3:1.0 to 1.0:0.6, and is more preferably in a range of from 0.4:1.0 to 0.9:1.0. In a preferred embodiment of this invention, the solasonine to solamargine ratio in the water-soluble extract is about 0.7:1.0.

Preferably, the extract is in a form of water-soluble particles with a nanoparticle size. More preferably, the extract is in a form of water-soluble particles with a particle size less than 1 µm.

The water-soluble extract according to this invention has been proved to have an inhibitory effect on the growth of tumor/cancer cells, in particular liver cancer cells, lung cancer cells, and breast cancer cells. Moreover, solasonine and solamargine obtained from the water-soluble extract according to the present invention have also demonstrated such inhibitory effect. Therefore, it is expected that the water-soluble extract prepared according to the present invention, and solasonine and solamargine contained therein, can find application in the preparation of an anti-tumor or anti-cancer composition.

Thus, this invention also provides a pharmaceutical composition, which comprises a water-soluble extract according to this invention, or solasonine and solamargine obtained from the water-soluble extract. Solasonine and solamargine purified from the water-soluble extract can also directly dissolve in water.

Optionally, the pharmaceutical composition according to this invention additionally comprises a pharmaceutically acceptable carrier that is widely employed in drug-manufacturing technology. The pharmaceutically acceptable carrier comprises one or more reagents, including, for example, water, saline, buffer solution, disintegrant, binder, excipient, lubricant, and absorption retardant.

The pharmaceutical composition according to this invention can be administered by parenteral or oral route in a suitable formulation, which includes sterilized aqueous solution or suspension, sterilized powder, tablet, capsule, cream, ointment, etc. The pharmaceutical composition according to this invention is preferably formulated to be suitable for injection, such as aqueous injection, powder injection, lyophilization product for injection, etc.

Optionally, the pharmaceutical composition of this invention can be administered alone or in combination with an additional anti-tumor/anti-cancer drug, e.g., mitomycin, adriamycin, actinomycin, cis-platin, etc.

Dosage amount and interval of the pharmaceutical composition according to this invention are dependent upon the following factors: severity of the disease to be treated, administering route, and the weight, age, health condition, and response of the subject to be treated. In general, the pharmaceutical composition according to this invention is administered orally or parenterally at a daily dosage of 2–6 mg/Kg in a single dosage form or a separate multi-dosage form.

The present invention will be illustrated in detail with reference to the following examples which are given for the purpose of illustration only and are not intended to limit the scope of the present invention.

EXAMPLE 1

Preparation of the Water-soluble Extract 500 g of ripe fruit of *Solanum incanum* L. was ground subsequent to addition of 1000 ml pure water. To the resultant aqueous mixture, 99.5% of acetic acid was added dropwise to adjust the pH value to 4.0, followed by shaking at room temperature for 12 hrs. A supernatant was obtained by centrifuging the aqueous mixture, and 33% $NH_4OH$ basic solution was added thereto dropwise to adjust the pH value of the supernatant to 9.0, and a precipitate was formed. The precipitate was obtained by conducting centrifugation at 4,500 rpm (Beckman Coulter, Avanti J-25, JA-14 Rotor), and the residual basic solution present therein was removed by washing the precipitate with water, followed by centrifugation at 4,500 rpm. The precipitate thus obtained was suspended in distilled water and subjected to lyophilization (Virtis, Freezemobile 12ES) to get 5 g of dried powder. The dried powder was largely suspended in aqueous solution, and cannot be directly dissolved in water or only a very small amount thereof may.

For preparation of an extract which can directly dissolve in water, 2 g of the dried powder was dissolved in 50 ml chloroform in reagent grade, followed by addition of 40 ml of 100% methanol and shaking to form a uniform suspension. A supernatant was obtained by centrifugation at 4,500 rpm or filtration. 70 ml of methanol:water solution (1:1) was added to the supernatant and mixed well. The mixture obtained was centrifuged at 12,000 rpm for 10 min. The resultant supernatant was taken out, and 120 ml distilled water was added thereto and shaken well. Meanwhile, the supernatant became murky. The supernatant was further centrifuged at 12,000 rpm for 10 min so as to remove the precipitate. The resultant supernatant was subjected to concentration under reduced pressure at 55° C. to remove methanol, followed by lyophilization to obtain dried powder.

The dried powder obtained at this stage can directly dissolve in distilled water to form a clear and transparent yellowish solution. If there is still some precipitate, it can be removed by centrifugation at 12,000 rpm for 10 min, and the resultant supernatant can be directly subjected to lyophilization to yield the water-soluble dried powder without conducting the step of concentration under reduced pressure.

In general, 800 mg water-soluble dried powder can be extracted from 500 g of the fruit of *Solanum incanum* L. Upon HPLC analysis, the major components of the water-soluble dried powder were observed to be solamargine and solasonine, in which the content of solamargine was higher than that of solasonine (see Example 2 and FIG. 1A).

In the aforesaid process of preparation, alternatively, the fruit can be immersed in 3% or 5% 1000 ml acetic acid aqueous solution and chopped. In addition, instead of conducting the step of shaking the aqueous mixture at room temperature for 12 hrs, the aqueous mixture formed may be shaken at 50° C. for 5 hrs, or at 80° C. for 2 hrs. Alternatively, sodium hydroxide aqueous solution can be used as a substitute for the $NH_4OH$ aqueous solution.

EXAMPLE 2

Identification of the Components of the Water-soluble Extract

High performance liquid chromatography (HPLC) was used to determine the major components of the water-soluble extract obtained from the process of the present invention.

Methodologies:

In this example, the high performance liquid chromatography (HPLC) employed was a 1100 model from Agilent Technologyies (Waldbronn, Germany), with a column of LiChroCART 2504 Lichropher 100 RP-18e (5 μm), and a size of 250 mm×4 mm; 60% acetonitrile/40% redistilled water (pH=2.8) was used as mobile phase; and flow rate was 1 ml/min. The standard specimens of solasonine and solamargine used in this experiment were provided by Professor Chun-Nan Lin, Department of Pharmacy, Kaohsiung Medical University, and the two standard specimens were obtained in accordance with the purifying procedure disclosed in Gan, K. H., Lin, C. N. and Won, S. J. (1993), *Journal of Natural Products* 56, 15–21.

Suitable amounts of the water-soluble extracts prepared from the fruits of *Solanum incanum* L. and *Solanum nigrum* according to the method of Example 1 were dissolved in pure water and subjected to HPLC analysis in accordance with the following conditions:

1. The water-soluble extract of *Solanum incanum* L. (25 μg), the water-soluble extract of *Solanum incanum* L. (25 μg) in combination with solasonine (5 μg), and the water-soluble extract of *Solanum incanum* L. (25 μg) in combination with solamargine (5 μg):

2. The water-soluble extract of *Solanum nigrum* (25 μg), the water-soluble extract of *Solanum nigrum* (25 μg) in combination with solasonine (10 μg), and the water-soluble extract of *Solanum nigrum* (25 μg) in combination with solamargine (10 μg); and 3. The water-soluble extracts of *Solanum incanum* L. in amounts of 50 g, 40 μg, 30 μg, 20 μg, 10 μg and 5 μg, respectively.

Results:

FIG. 1A shows a HPLC spectrum of the water-soluble extract from the fruit of *Solanum incanum* L. Compared with the retention time shown in FIGS. 1B and 1C, it is noted that the first peak in FIG. 1A corresponds to solasonine and the second one corresponds to solamargine, and that the content of solamargine is higher than that of solasonine.

Figure 2A:
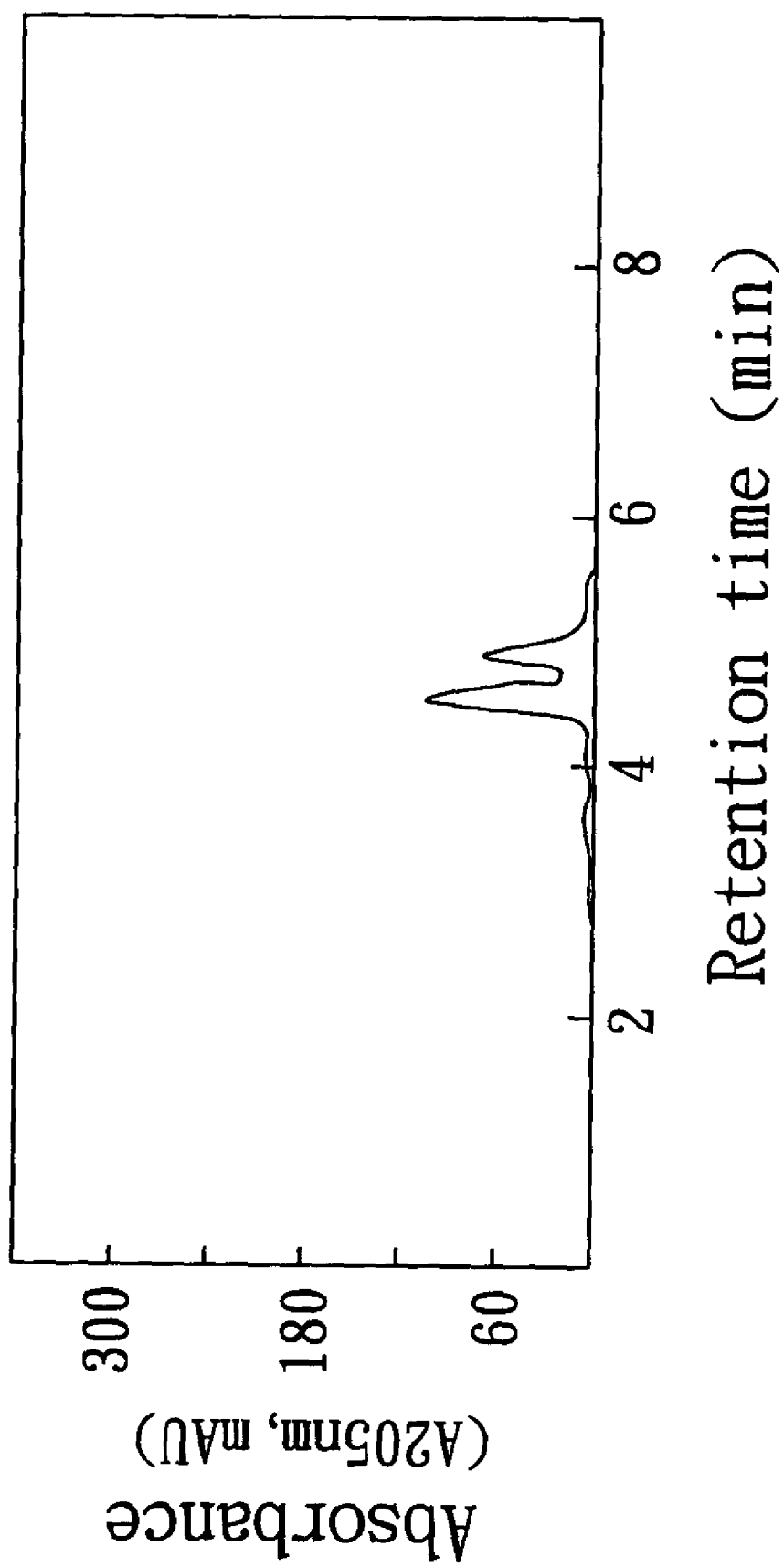
FIG. 2A shows HPLC spectrum of the water-soluble extract (25 μg) obtained from *Solanum nigrum*.
Figure 2B:
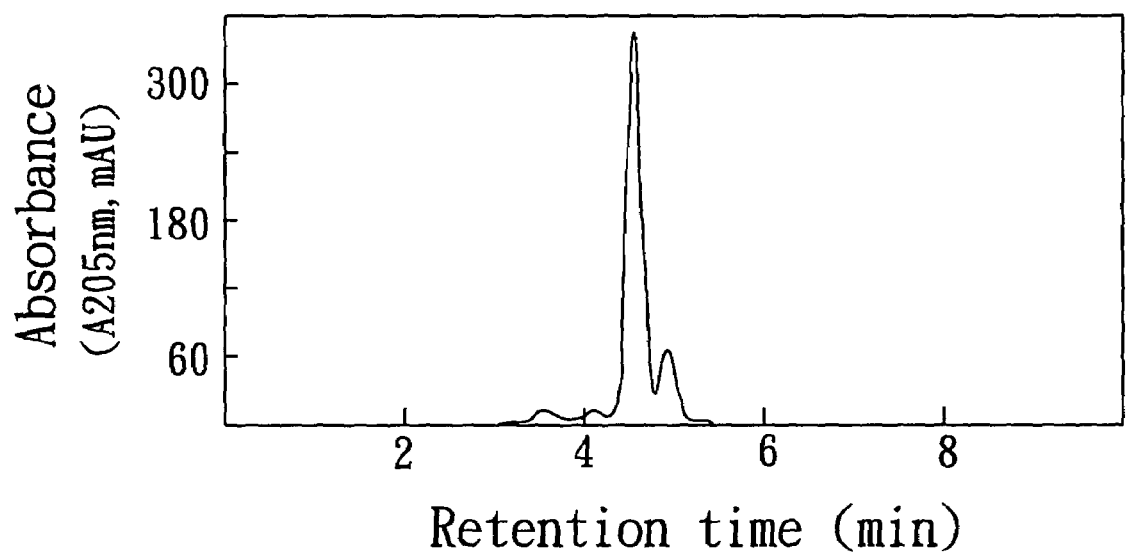
FIG. 2B shows HPLC spectrum of the water-soluble extract (25 μg) obtained from *Solanum nigrum* in combination with solasonine (5 μg)
Figure 2C:
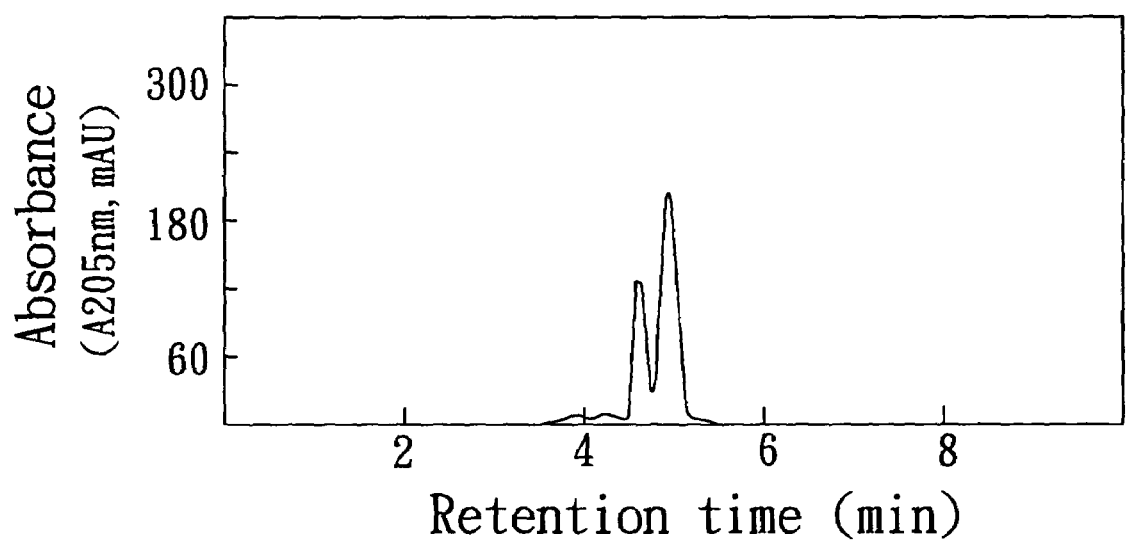
FIG. 2C shows HPLC spectrum of the water-soluble extract (25 μg) obtained from *Solanum nigrum* in combination with solamargine (5 μg)
Figure 3A:
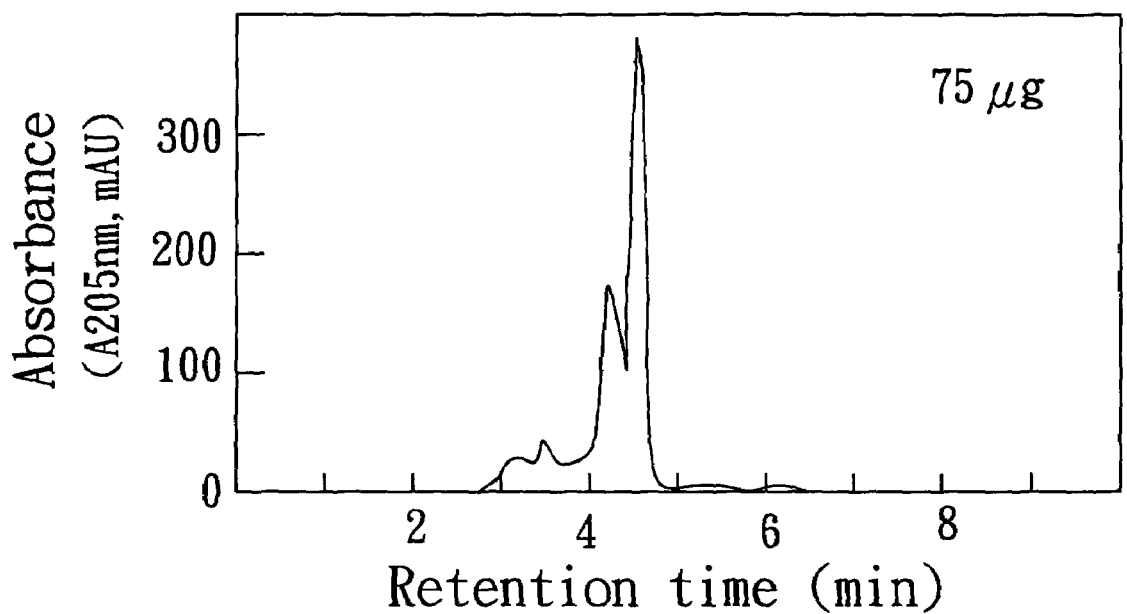
FIGS. 3A–3F are HPLC spectra of the water-soluble extract obtained from *Solanum incanum* L. with various concentrations.
Figure 3B:
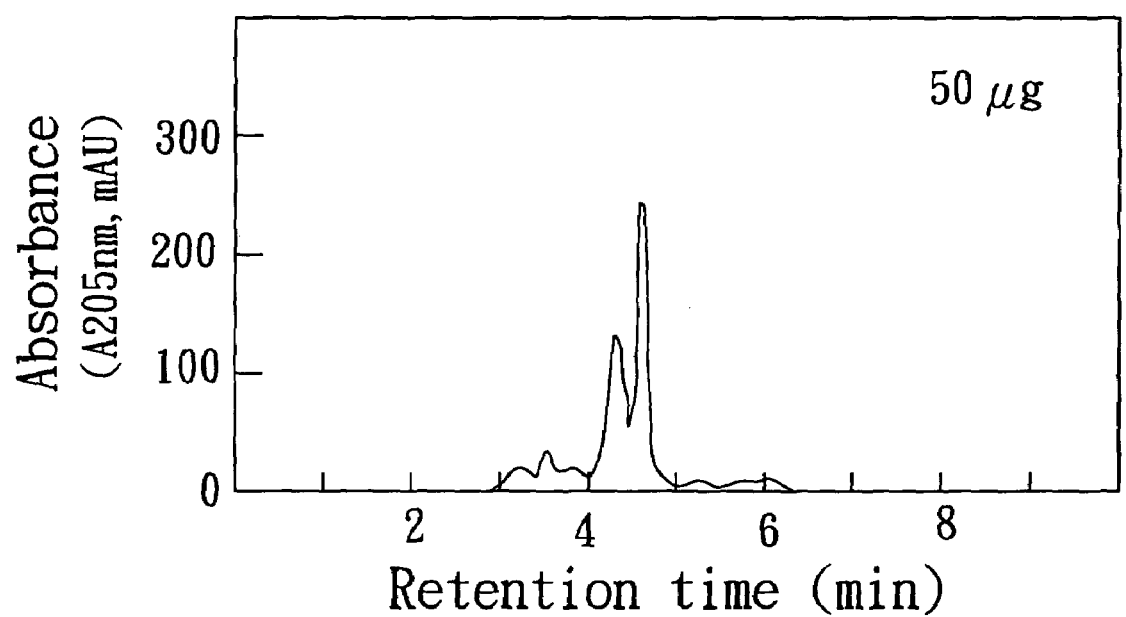
Figure 3C:
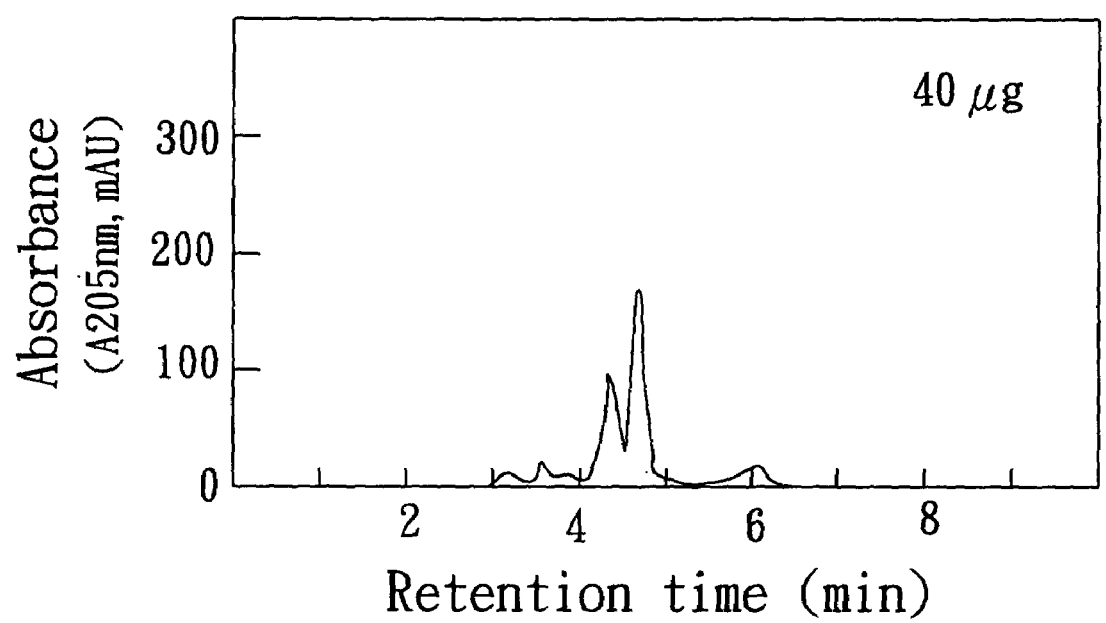
Figure 3D:
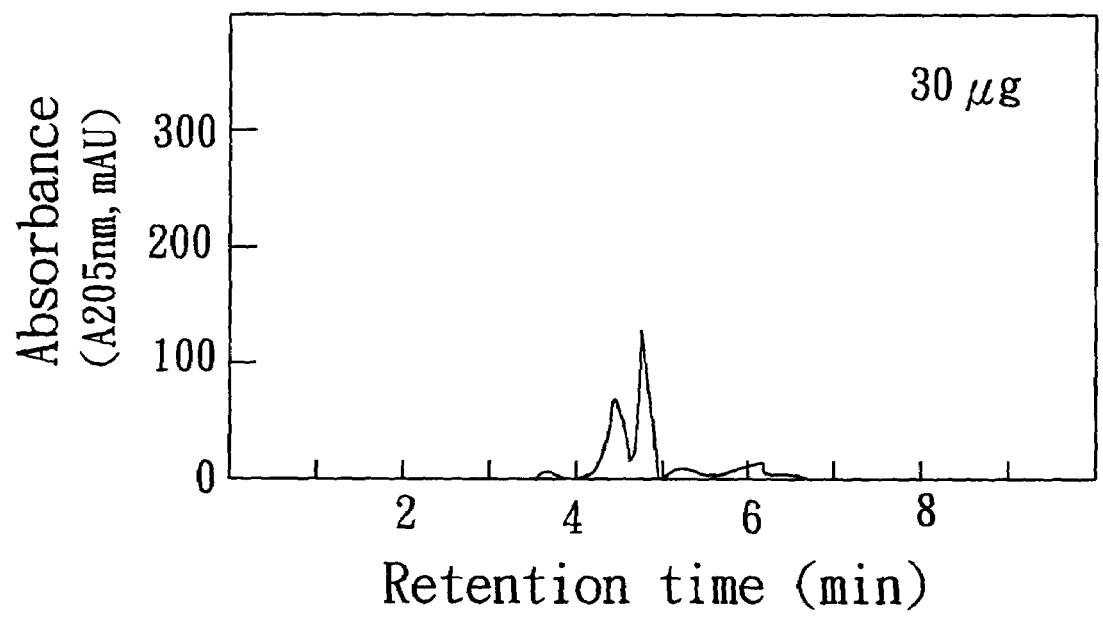
Figure 3:
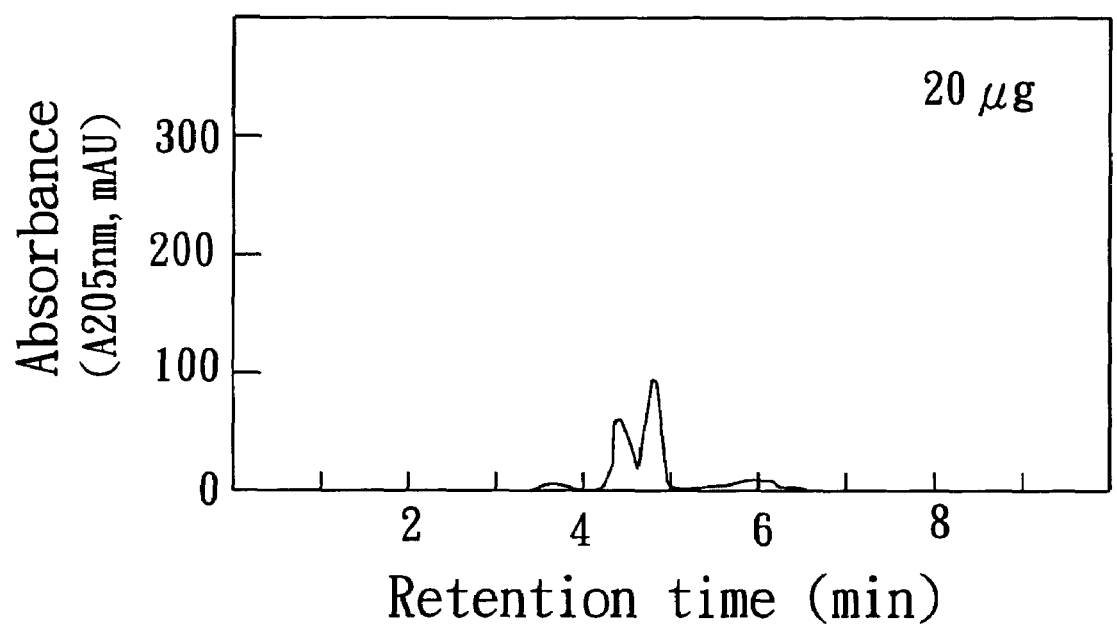
Figure 3:
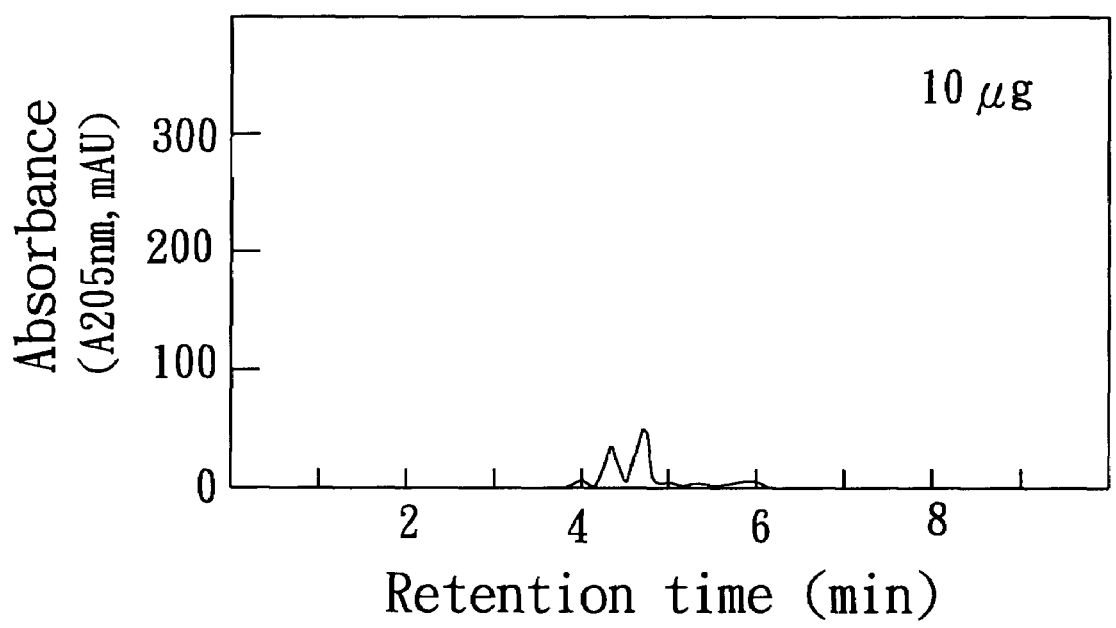

Referring to FIGS. 2A–2C, the HPLC spectra showed that the water-soluble extract from the fruit of *Solanum nigrum* also gave two peaks that correspond to solasonine and solamargine. However, the difference between the water-soluble extract from the fruit of *Solanum nigrum* and that of *Solanum incanum* resides in that, in *Solanum nigrum*, the content of solasonine was higher than that of solamargine.

In addition, as shown in FIGS. 1A–1C and FIGS. 2A–2C, the water-soluble extract according to this invention did not include solasodine, and was obviously different from the extract disclosed in EP 0 020 029 A1.

FIGS. 3A–3F are HPLC spectra of the water-soluble extract from *Solanum incanum* L. in the amounts of 75 μg, 50 μg, 40 μg, 30 μg, 20 μg, and 10 μg, respectively. It is found that the peak values of the two major components of the water-soluble extract of *Solanum incanum* L. would fluctuate in proportion to the concentrations of the water-soluble extract.

As to the proportion of solasonine and solamargine, it can be estimated by automated integration using a computer program (Agilent ChemStation Integrator Algorithm) in accordance with the HPLC eluting spectrum. If a pointed or round peak form appeared in the spectrum, such variation may be due to factors of fruit maturity and the season. Based upon 26 repeated experiments, it was found that the water-soluble extract of *Solanum incanum* L. has a solasonine to solamargine ratio within the range from about 0.3:1.0 to about 1.0:1.0, and mainly within the range from 0.4:1.0 to 0.9:1.0.

From the experimental results, the applicant found that the water-soluble extract according to this invention essentially consists of at least 60% to 95% (preferably more than 75%) of solasonine and solamargine.

Figure 4:
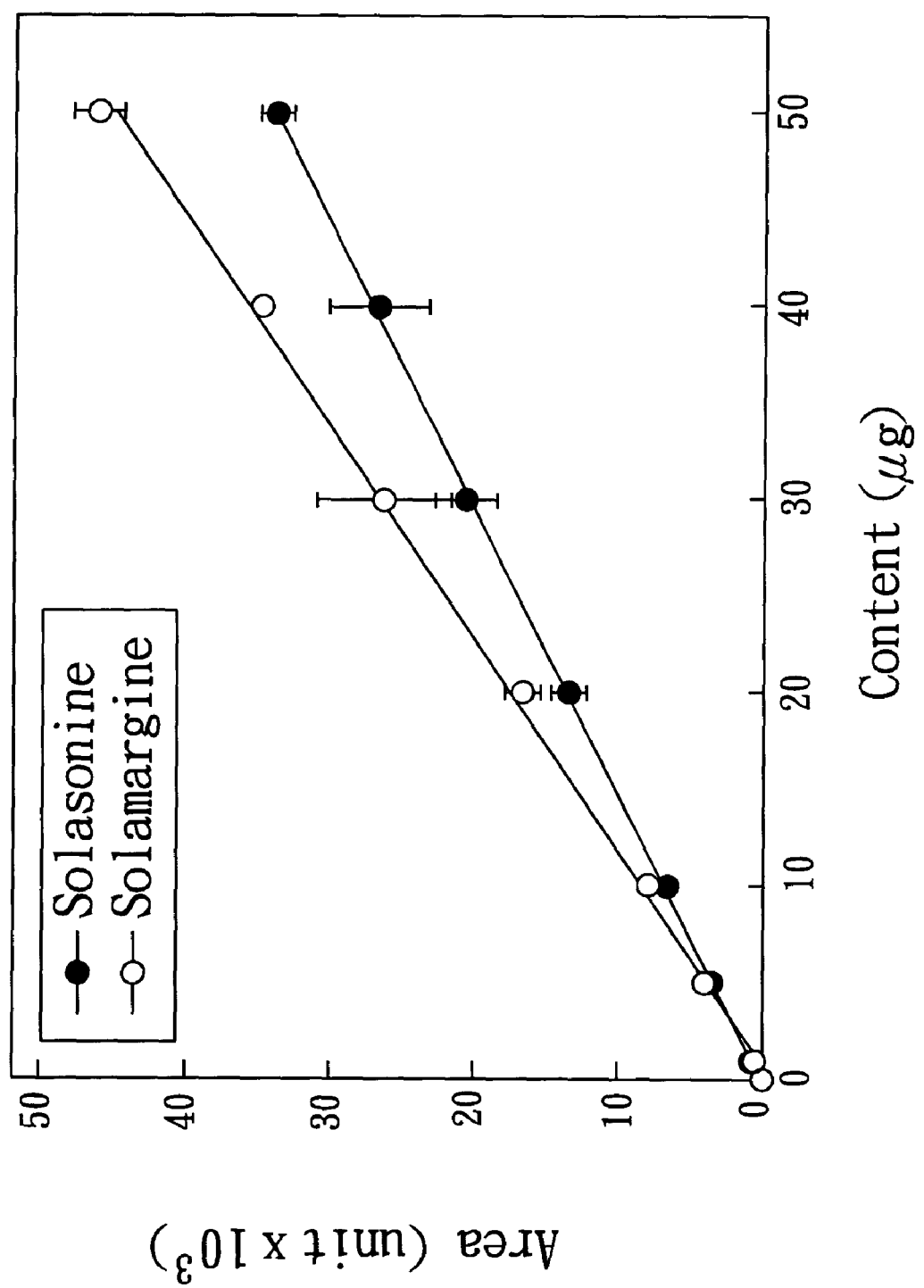
FIG. 4 is a graph indicating the quantitative standards of the major components in the water-soluble extract of *Solanum incanum* L. estimated from HPLC spectra of FIGS. 3A–3F.
Figure 5A:
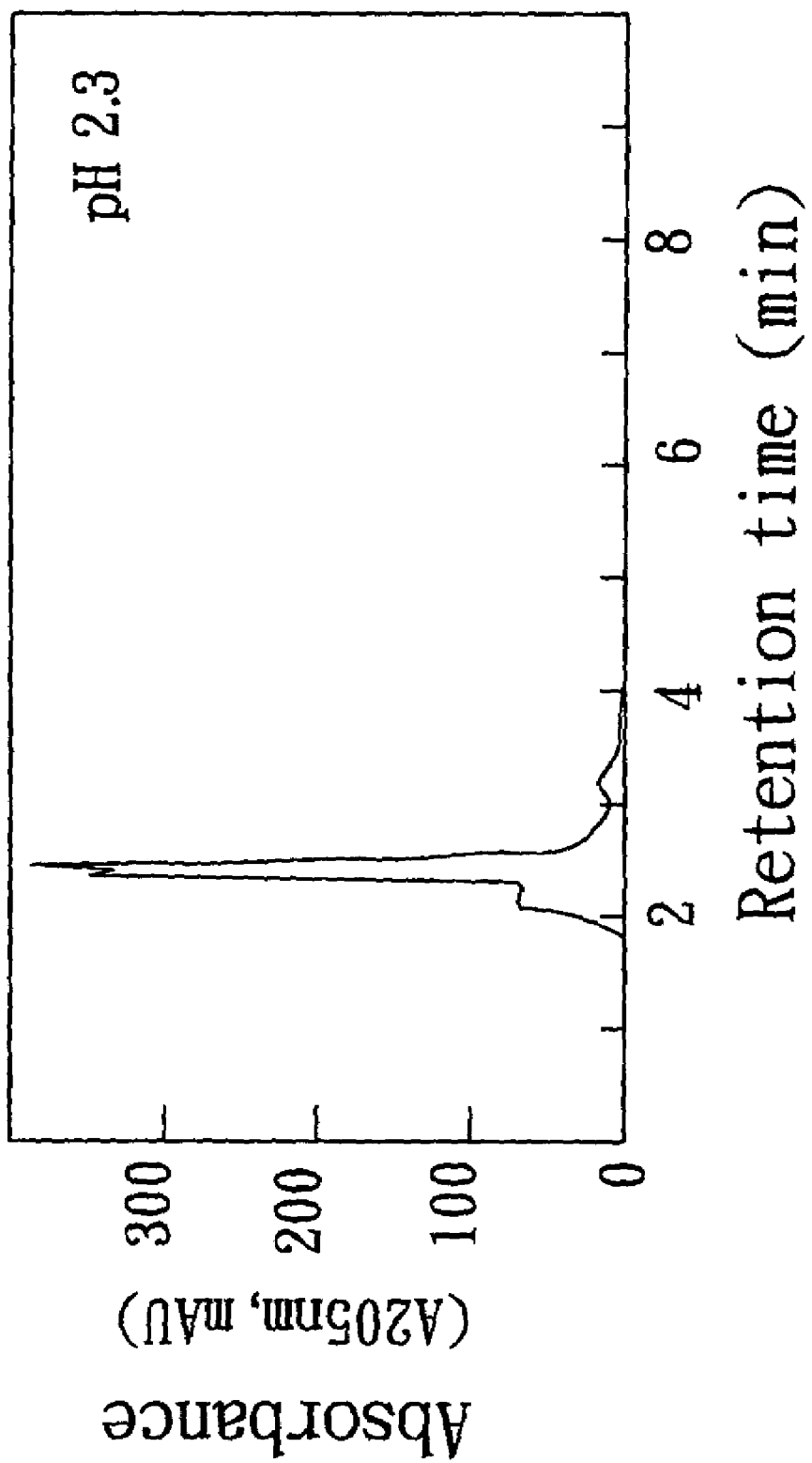
FIGS. 5A–5E are HPLC spectra of the water-soluble extract obtained from *Solanum incanum* L. at various pH values.
Figure 5B:
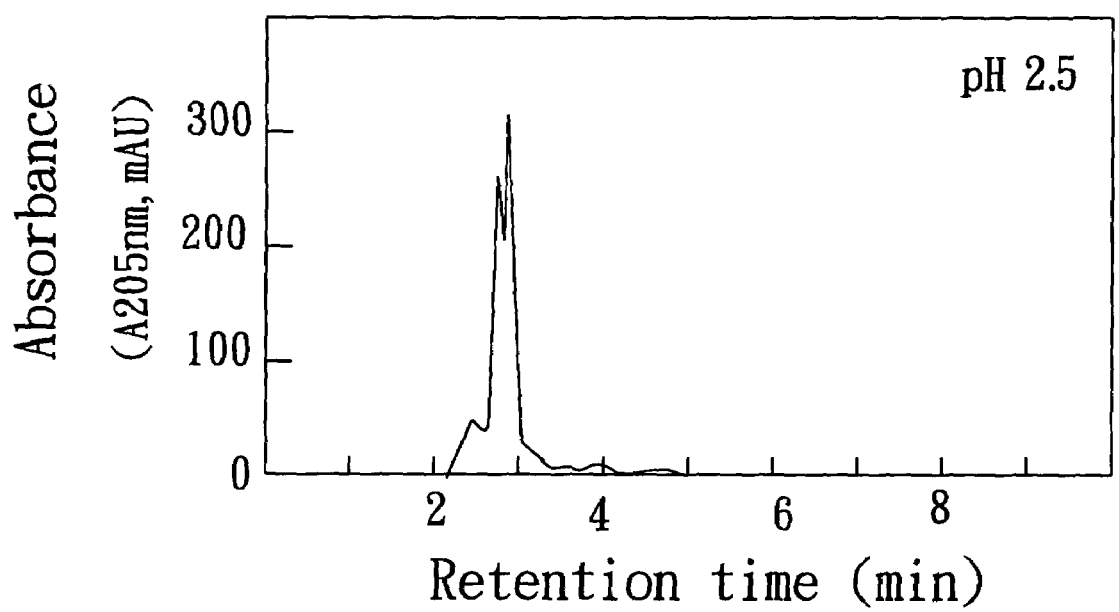
Figure 5C:
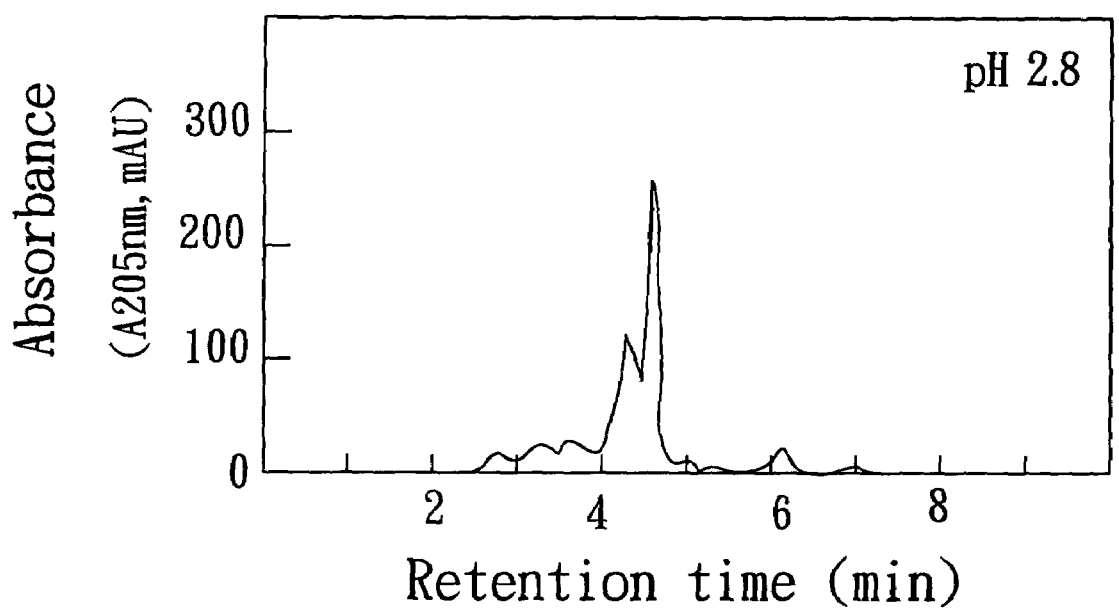
Figure 5D:
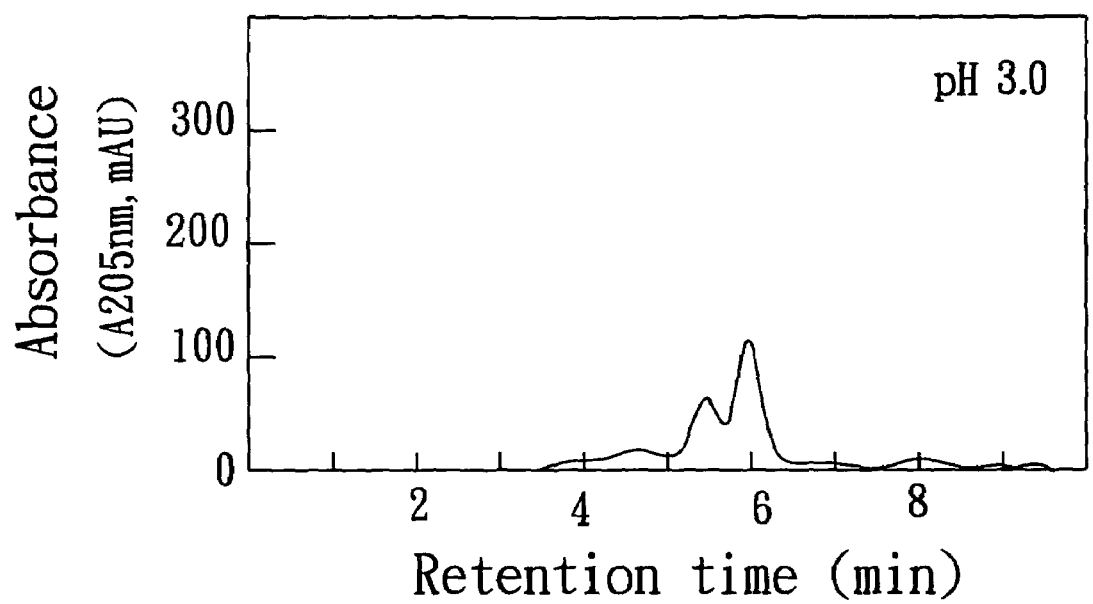
Figure 5E:
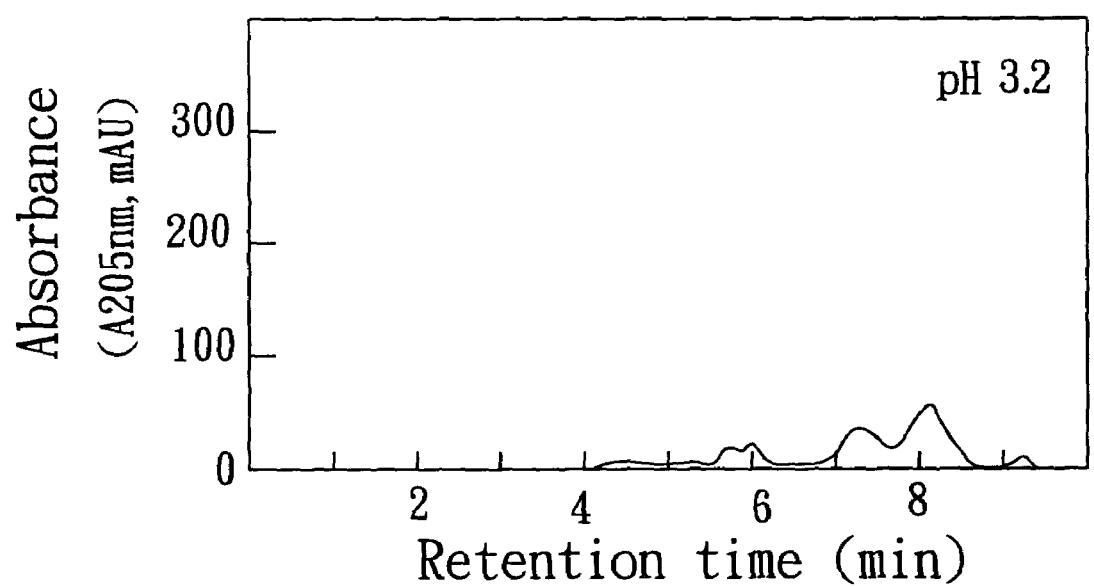

The applicant also found that the content and proportion of solasonine and solamargine varied with the concentration of the water-soluble extract used in HPLC analysis in a linear relationship. FIG. 4 is a graph showing calibration curves plotted using linear regression, in which seven concentrations of the water-soluble extracts of *Solanum incanum* L. underwent HPLC analysis in triplicate, and the values, means ±SD, were calculated from the integral of HPLC peak area of the two major components. The result shown in FIG. 4 clearly indicated that the peak values of solasonine and solamargine rose and dropped in a linear relationship with the concentration of the water-soluble extract. Therefore, the two components, solasonine and solamargine, can be used as an index component for quality control of the water-soluble extract according to this invention.

In addition, solamargine and solasonine capable of being dissolved directly in water can be further purified from the water-soluble extract of this invention using the aforesaid HPLC condition.

EXAMPLE 3

The Effect of pH on Elution of the Water-soluble Extract

Methodologies:

In order to determine the influence of pH on elution of the water-soluble extract, the water-soluble extract (40 μg) of *Solanum incanum* L. prepared using the method of Example 1 was subjected to HPLC analysis using the same equipment used in Example 2 under the following HPLC condition:

1. Column: LiChroCART 250-4 Lichropher 100 RP-18e (5 μm), 250 mm×4 mm; and
2. Mobile phase: 60% acetonitrile/40% redistilled water, pH adjusted to 2.3, 2.5, 2.8, 3.0 and 3.2.

Results:

FIGS. 5A–5E show the HPLC spectra of the water-soluble extract from *Solanum incanum* L. under different pH values. As shown, the retention time of the major component of the water-soluble extract was delayed by rise in pH value of the mobile phase. Although the elution profiles slightly changed, the two-component peak profile was still maintained.

EXAMPLE 4

Comparison in Particle Size of the Water-soluble Extract

This example was performed to compare the difference in particle size between the water-soluble extract from *Solanum incanum* L. prepared using the method of this invention and that obtained using the method disclosed in Example 2 of EP 0 020 029 A1.

Methodologies:

50 mg of the water-soluble extract prepared from *Solanum incanum* L. according to this invention, and 50 mg of the extract prepared from *Solanum incanum* L. according to the method disclosed in Example 2 of EP 0 020 029 A1, were respectively dissolved in 50 ml distilled water, and subjected to a particle size analysis using particle size analyzer (Beckman Coulter LS 230, Coulter Corporation, Miami, USA).

Figure 6:
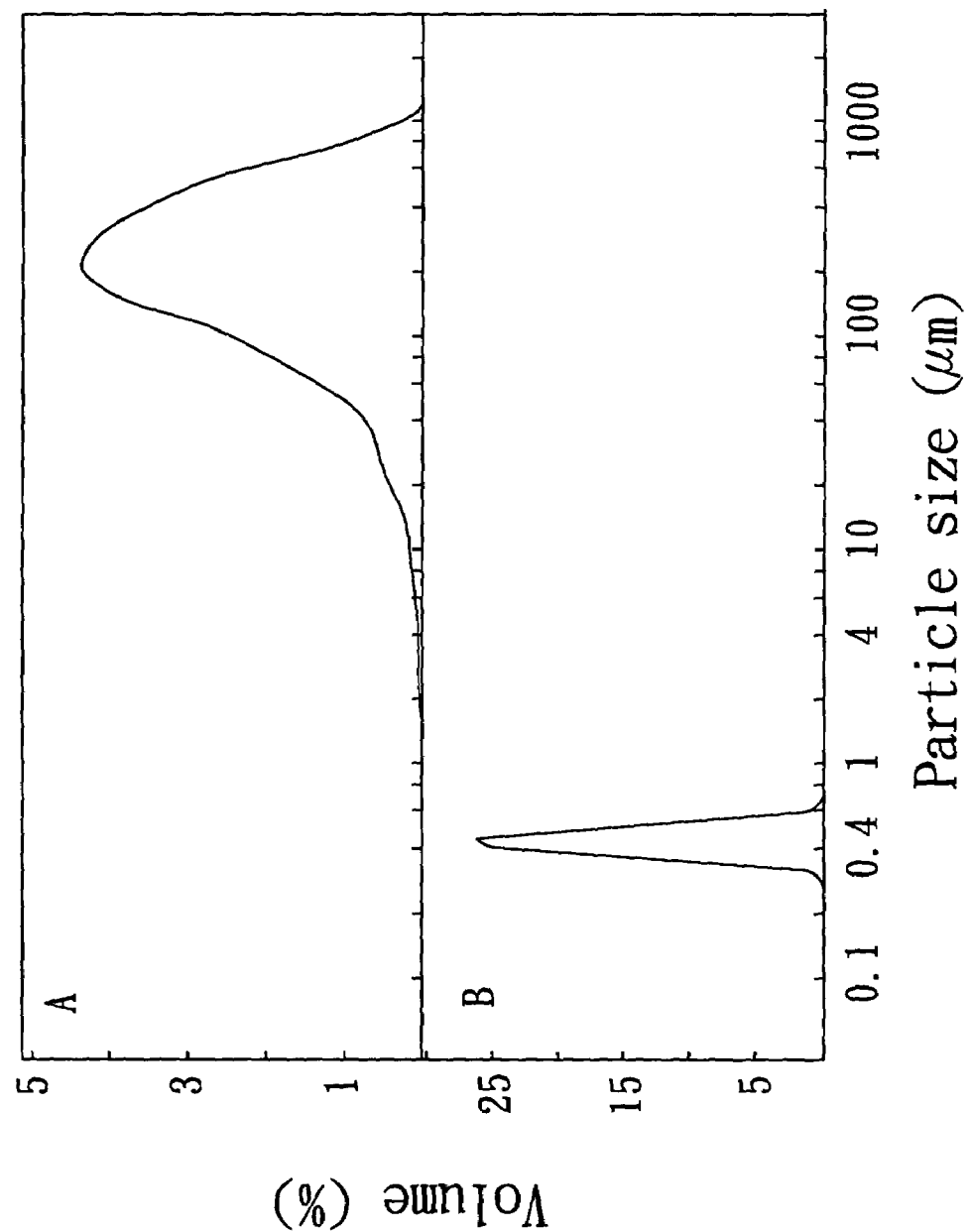
FIG. 6 shows the comparative results in the particle size of the water soluble extracts obtained from *Solanum incanum* L. according to the present invention and from the method of EP 0 020 029 A1 respectively.

Results:

Referring to FIG. 6, the average particle size of the extract prepared from *Solanum incanum* L. according to the method disclosed in Example 2 of EP 0 020 029 A1 was 238.2 μm and the particle size distribution was in a range of from 1.8 μm to 1500 μm, and there was a large amount of insoluble precipitate in the aqueous solution (see FIG. 6A). On the contrary, the average particle size of the water-soluble extract prepared from *Solanum incanum* L. according to this invention was 0.418 μm, and the particle size distribution was in a range of from 0.28 μm to 0.65 μm (see FIG. 6B). The extract according to this invention can be completely dissolved in water.

EXAMPLE 5

Comparison in Solubility of the Water-soluble Extract

This exemplary experiment was performed to compare the difference in water-solubility between the water-soluble extract from *Solanum incanum* L. prepared using the method of this invention and that obtained using the method disclosed in Example 2 of EP 0 020 029 A1.

Methodologies:

5 mg of the water-soluble extract prepared from *Solanum incanum* L. according to this invention, and 5 mg of the extract prepared from *Solanum incanum* L. according to the method disclosed in Example 2 of EP 0 020 029 A1, were respectively dissolved in 2 ml distilled water, and centrifuged at 12,000 rpm to obtain a supernatant. 20 μl supernatant was taken out and subjected to HPLC analysis according to the procedure disclosed in Example 2 of this invention.

Figure 7A:
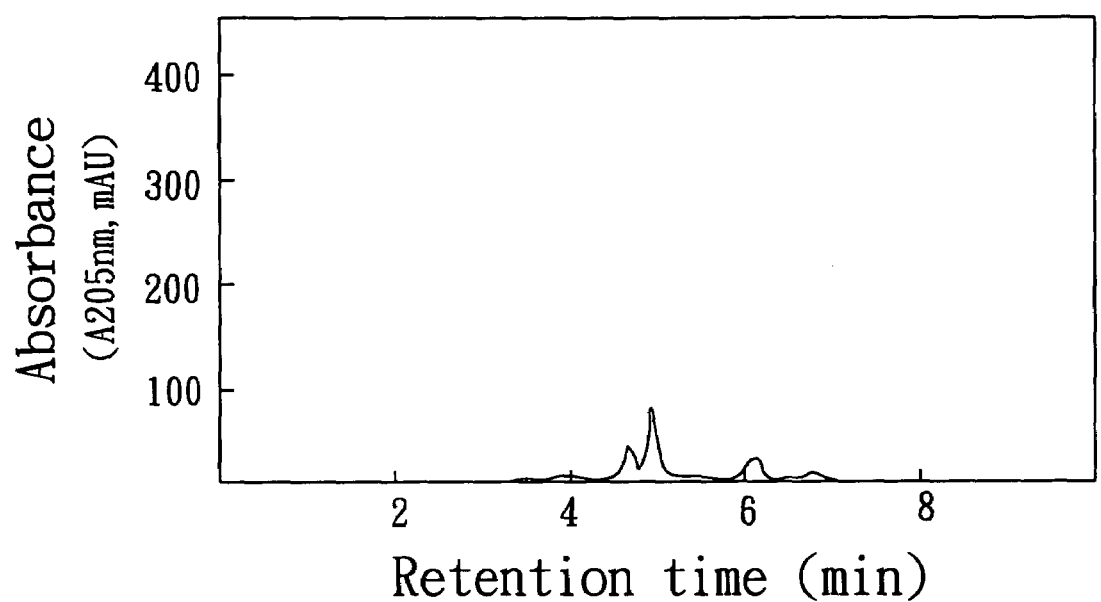
FIGS. 7A and 7B are HPLC spectra of the water-soluble extracts obtained from *Solanum incanum* L. according to the present invention and from the method of EP 0 020 029 A1, wherein 50 μg of the water-soluble extracts obtained from the two methods are dissolved in water, followed by HPLC analysis.
Figure 7B:
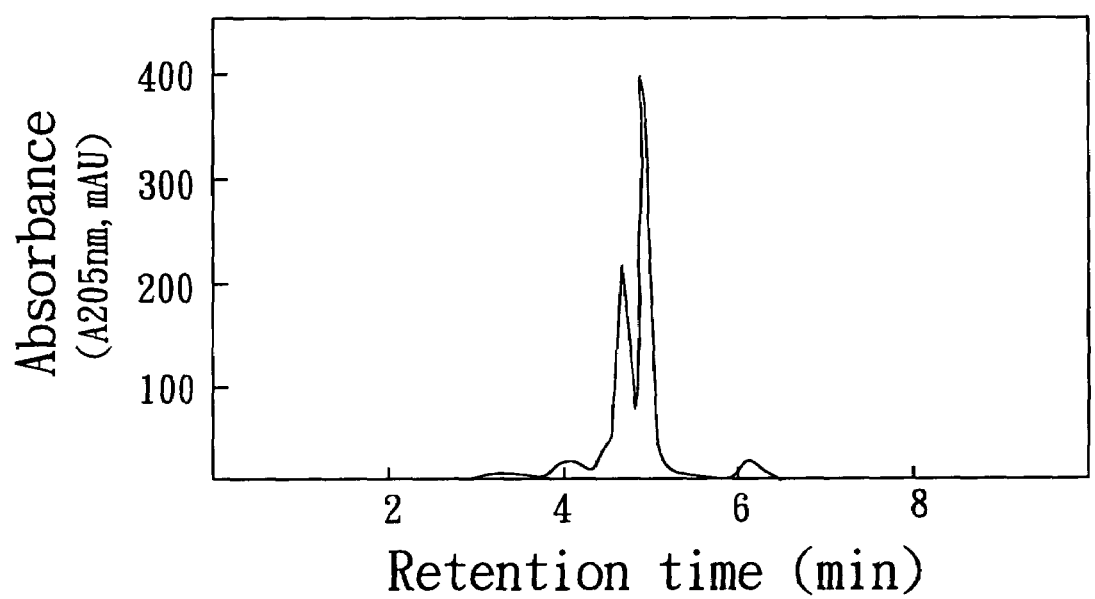

Results:

FIGS. 7A and 7B are graphs respectively showing the water-solubility of the extract prepared from *Solanum incanum* L. according to the method disclosed in Example 2 of EP 0 020 029 A1 (FIG. 7A) and of the water-soluble extract prepared from *Solanum incanum* L. according to this invention (FIG. 7B). As shown, the water-soluble extract prepared from *Solanum incanum* L. according to this invention has better water solubility.

It is apparent from the above Examples and Figures that, as compared with the extract prepared using a conventional method, the water-soluble extract prepared from the plant of *Solanum* genus according to this invention indeed can dissolve in water to form a clear and transparent aqueous solution. This may be due to the fact that the water-soluble extract prepared from the plant of *Solanum* genus according to this invention has a nanoparticle size, particularly, less than 1 μm. Accordingly, it is expected that the water-soluble extract prepared from a plant of *Solanum* genus according to this invention is suitable for use in the preparation of a medicament comprising steroidal alkaloids, especially a medicament for cancer treatment.

Accordingly, in order to prove the bio-activity of the water-soluble extract prepared from a plant of *Solanum* genus according to this invention, the water-soluble extract of *Solanum incanum* L. prepared in Example 1 of this invention was tested for pharmacological effect.

Pharmacological Experiment 1.

Anti-cancer Activity of the Water-soluble Extract in vitro

In order to determine whether the water-soluble extract obtained from the plant of *Solanum* genus according to this invention has anti-cancer activity, the principal cancer cells of Hep3B, H441, and MCF-7 were used as analytic targets, in which Hep3B and H441 were purchased from American Type Culture Collection (ATCC, P.O. Box 1549, Manassas, Va. 20108 USA), and MCF-7 was purchased from Food Industry Research and Development Institute (331 Shih-Pin Road, Hsinchu, 300 Taiwan R.O.C.).

Methodologies:

Hep3B was incubated in Dulbecco's Modified Eagle's medium (DMEM), while H441 and MCF-7 were incubated in RPMI-1640, both of the media containing 10% fetal bovine serum and 40 mg/L gentamycin.

The cytotoxicity of cancer cells was determined using tetrazolium salt assay (MTS, Mosmann. T., 1983, *Immunol. Meth.*, 65, 55–63), which was conducted for the calorimetric determination of cell viability according to the manufacturer's procedures (CellTiter 96™ AQ, Promega, Madison, USA).

Cells were seeded at $1 \times 10^4$ cells/well in a 96-well plate and incubated in 5% $CO_2$ incubator at 37° C. for at least 16 hrs. The water-soluble extract from *Solanum incanum* L. was dissolved in sterile injection water to give different test concentrations, which were added to each cancer-cell incubating medium in the well, and allowed to react for 12 hrs. 20 μl MTS was then added to each well, and the solution was allowed to react for 3 hrs. Upon completion of the reaction, absorbency in each well was determined at 490 nm by using ELISA reader 312e, Bio-TEK. Each value was expressed as means ±SD from three experiments.

Figure 8A:
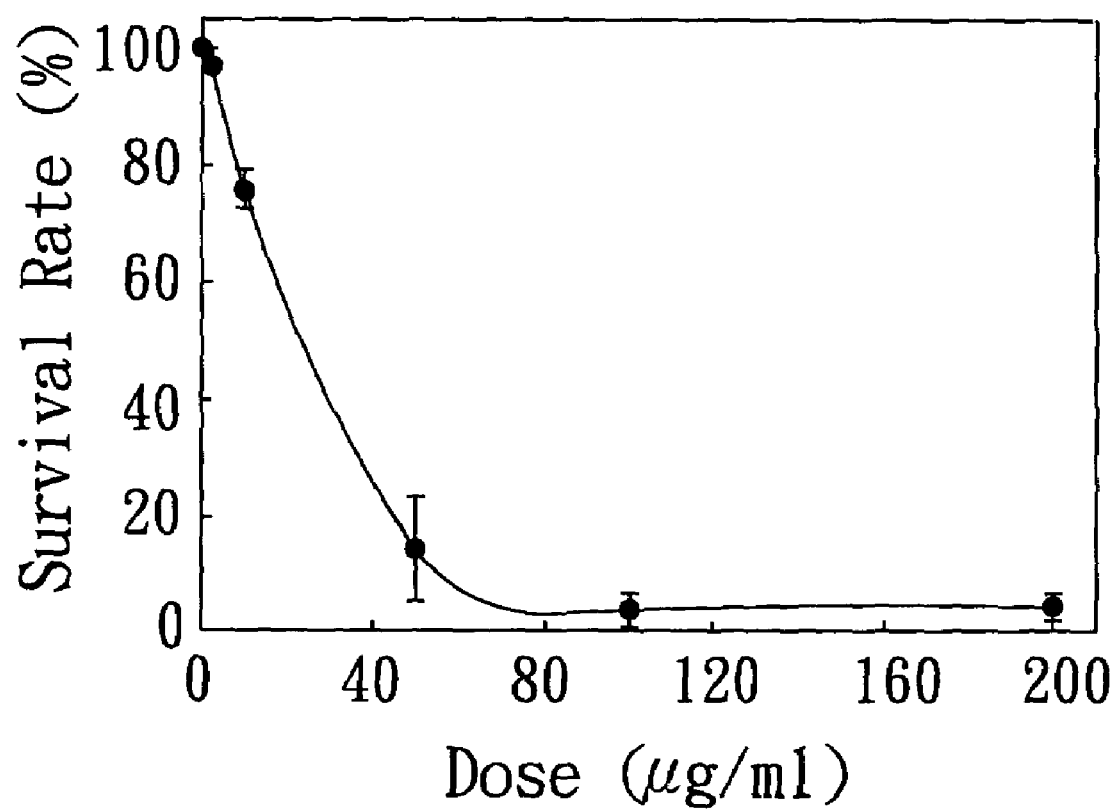
FIGS. 8A–8C are graphs indicating the inhibitory effect of serial dosages of the water-soluble extract obtained from *Solanum incanum* L. according to the present invention on the growth of human liver cancer, lung cancer, and breast cancer cells.
Figure 8:
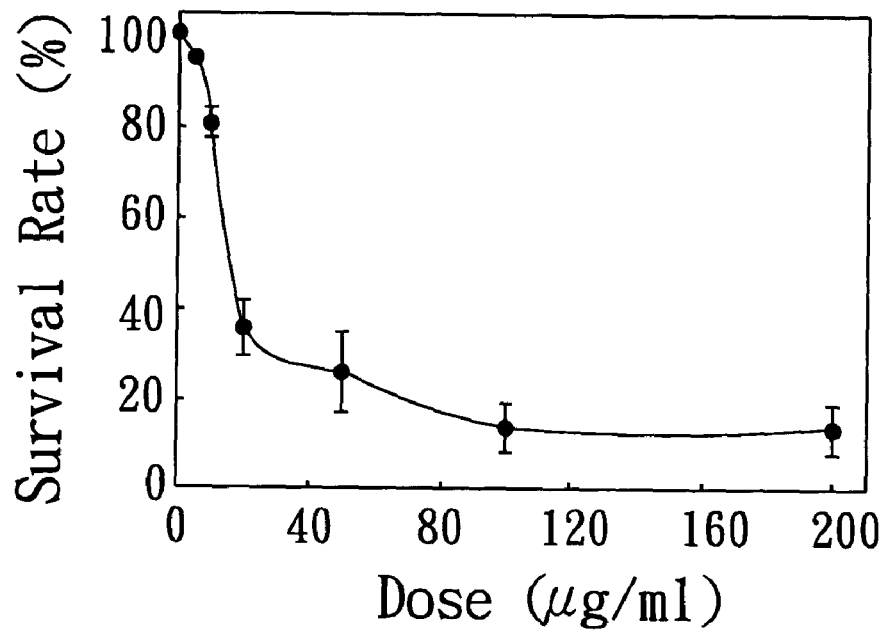
Figure 8:
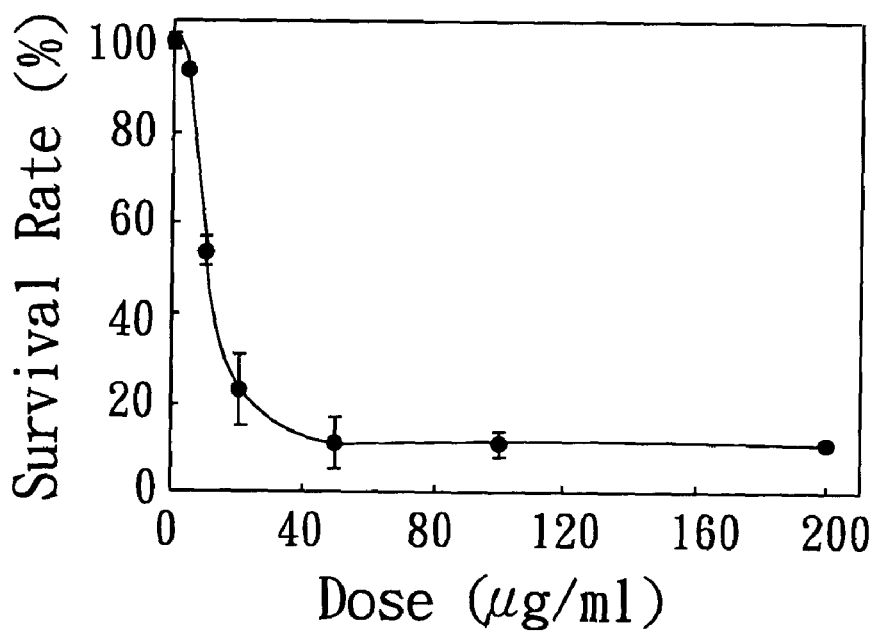

Results:

FIGS. 8A–8C are graphs showing the effect of the water-soluble extract prepared from *Solanum incanum* L. according to this invention on inhibiting the growth of Hep3B, H441, and MCF-7. It was observed that the water-soluble extract prepared from *Solanum incanum* L. according to this invention effectively inhibited the growth of these cancer cells.

Pharmacological Experiment 2.

Determination of the Effect of Water-soluble Extract Prepared from *Solanum incanum* L. According to this Invention on Gene Regulating Mechanism in Lung Cancer Cells by Using Gene Chip In order to understand the effect of the water-soluble extract prepared from *Solanum incanum* L. according to this invention on gene regulation in cancer cells so as to blaze the trail in the development and research on cancer treatment and to assist in the research on carcinogenic factors and the development of an effective anti-cancer medicament, this experiment was performed to determine the regulating effect of the water-soluble extract of this invention by gene chip technology.

In this experiment, a commercially available gene chip array (SuperArray Inc., Bethesda, Md., USA) was used to determine the effect of the water-soluble extract prepared from *Solanum incanum* L. according to this invention on gene regulation in H441 cancer cells.

Firstly, the RNA samples were isolated from cancer cells treated for 2 hrs with the water-soluble extract (100 μg/ml) prepared from *Solanum incanum* L. according to this invention and from cancer cells not treated with the extract (control group). Labeled cDNAs were generated by conducting reverse transcription using [$^{32}$P]-dCTP, which could be used as a probe for hybridization with DNA fragments on the gene chip array (SuperArray Inc., Bethesda, Md., USA). The reacted gene chip array was exposed to x-ray film using autoradiography.

Figure 9:
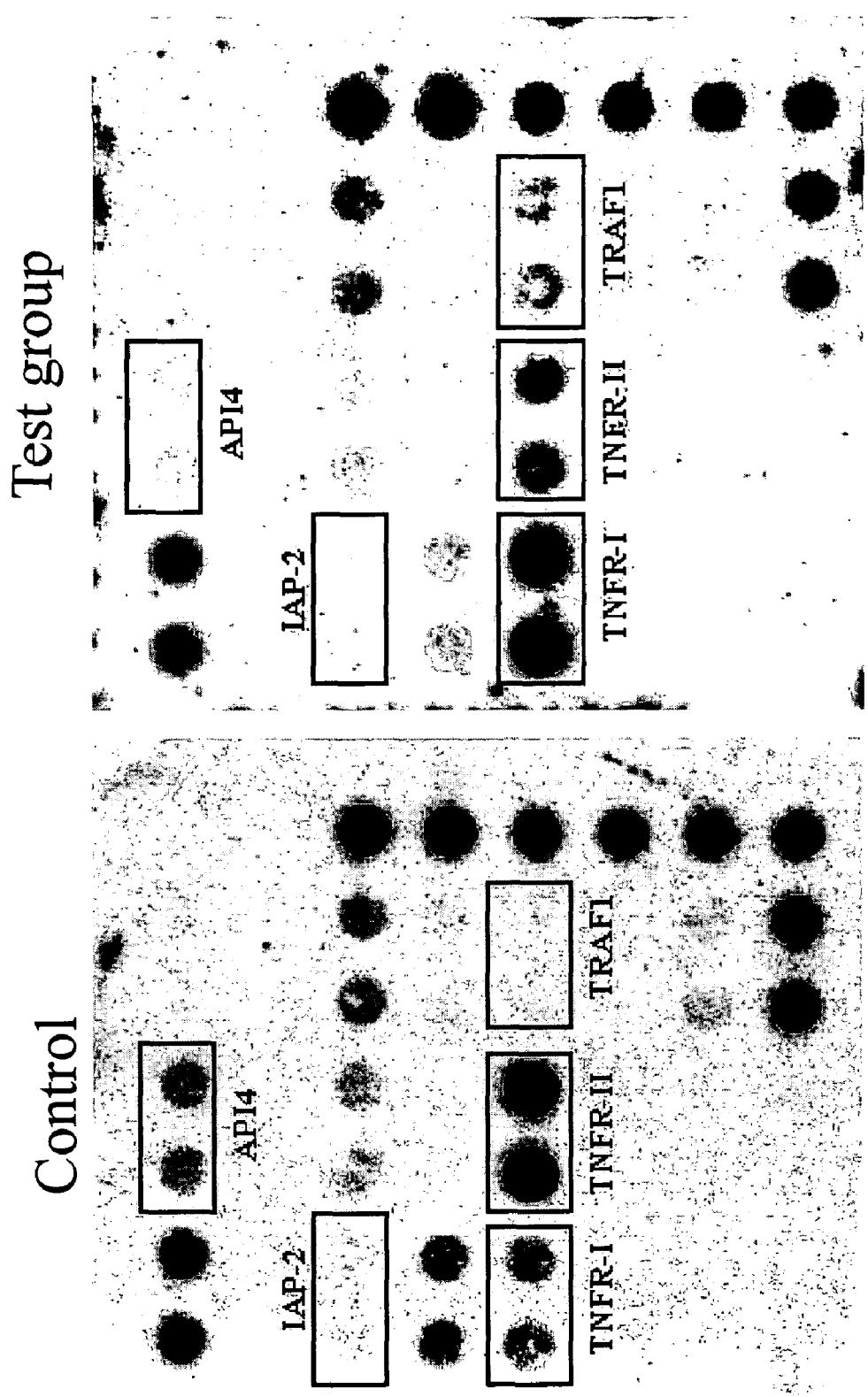
FIG. 9 is a set of graphs showing the autoradiography results on a gene chip, which indicate the effect of the water-soluble extract obtained from *Solanum incanum* L. according to the present invention on gene regulation of lung cancer cells, in which RNA samples were isolated from the lung cancer cells treated with the water-soluble extract (100 μg/ml) obtained from *Solanum incanum* L. for 2 hrs, and subjected to reverse-transcription using [$^{32}$P]-dCTP to produce labeled cDNA, and the labeled cDNA thus obtained is hybridized to DNA fragments on the gene chip array, followed by autoradiography to X-ray film.

Results:

Referring to FIG. 9, after H441 was treated with the water-soluble extract prepared from *Solanum incanum* L. according to this invention for two hrs, gene expression of tumor necrosis factor receptor I (TNFR-1) and TNF receptor-associated factor-1 (TRAF-1) positively associated with the death of cancer cells was up-regulated, whereas gene expression of Inhibitor of apoptosis protein 2. (IAP-2) and apoptosis inhibitor 4 (API-4) which inhibit cell death was down-regulated due to the influence of the extract. Thus, it can be seen that the water-soluble extract prepared from *Solanum incanum* L. according to this invention is capable of initiating the gene expression of TNFR-1 and TRAF-1.

Pharmacological Experiment 3.

Effect of the Water-soluble Extract Prepared from *Solanum incanum* L. According to this Invention on Cell Cycle of the Cancer Cells Flow cytometry ("FACScan"; Becton Dickinson Corp.) was used to determine the change of cell cycle of cancer cells before and after the cells were treated with the water-soluble extract prepared from *Solanum incanum* L. according to this invention.

Methodologies:

First, after incubating $1 \times 10^6$ cancer cells in 35 mm plate for 16 hrs, the water-soluble extract (30 μg/ml) prepared from *Solanum incanum* L. according to this invention was added to each plate and allowed to react for 0, 1, 3, 5, and 8 hrs. When the respective reaction times were up, the cells were trypsinized with 1× trypsin and the supernatant and medium were collected. The cell-containing supernatant was transferred into a 15 ml centrifuge tube and centrifuged at 1000 rpm for 5 minutes to obtain the pellet. After adding 300 μl 1× PBS and mixing well, 300 μl cell suspension was transferred into a microtube, and fixed in 700 μl absolute alcohol. The fixed cells were allowed to stand in 4° C. refrigerator for at least 30 minutes and centrifuged at 4° C., 1200 rpm for 5 min. After centrifugation, a supernatant was obtained and mixed well. To the supernatant 445 μl of 1×PBS solution was added and mixed well, followed by addition of 5 μl of RNase (10 mg/ml) to digest RNA. The cells were permeabilized with 50 μl of 10% Triton-X100 and incubated in an incubator at 37° C. for 1 hr, followed by centrifugation. A supernatant was taken out and mixed well with 495 μl of PBS solution. The cells were stained with 5 μl of propidium iodide (5 mg/ml) in the dark at 4° C. for 15–30 min, followed by filtration and analysis.

Determination of Cell Cycle:

The cells adhering to the filter were suspended well in 1× PBS solution and introduced into Flow Cytometry (Beckman-Coulter FACScan) at 100 cells/sec. 10,000 cells were analyzed at a time. The cells were passed through pores with 75 μm radius to produce current pulse signals in proportion to the cell volume. The cells were excited by a laser beam of argon ion at 488 nm to emit fluorescence. Data obtained was used to analyze DNA content in combination with Winmdi software so as to determine the cell cycle.

Results:

Table 1 shows the changes of cell cycle of Hep3B, H441, and MCF-7 treated with the water-soluble extract prepared from *Solanum incanum* L. according to this invention, in which rise of sub-G1 peak indicated that the cancer cells were undergoing apoptosis induced by the water-soluble extract.

As shown in Table 1, sub-G1 peak of the cell cycle in cancer cells increased drastically within 1 hr, and it increased with an increase in reaction time. The cancer cells died of breakage of cell membrane as a result of high dosages of the extract. It has thus been shown that the water-soluble extract prepared from *Solanum incanum* L. according to this invention can initiate the apoptosis mechanism of the three kinds of cancer cells.

TABLE 1

Effect of the water-soluble extract prepared from *Solanum incanum* L. according to this invention on cell cycle of Hep3B, H441, and MCF-7

| | Sub-G1 | | G0/G1 | | S | | G2/M | |
|---|---|---|---|---|---|---|---|---|
| Time (hr) | means ± S.D | % | means ± S.D | % | means ± S.D | % | means ± S.D | % |
| Live cancer cells | | | | | | | | |
| 0 | 5.5 ± 0.2 | 100 | 58.8 ± 0.3 | 100 | 17.4 ± 0.3 | 100 | 18.0 ± 0.5 | 100 |
| 1 | 38.3 ± 0.6 | 246 | 31.9 ± 0.9 | 64 | 15.1 ± 0.1 | 87 | 14.6 ± 0.4 | 81 |
| 3 | 69.5 ± 0.4 | 446 | 15.4 ± 0.3 | 31 | 9.9 ± 0.2 | 57 | 5.6 ± 0.2 | 31 |
| 5 | 90.7 ± 0.7 | 581 | 4.3 ± 0.3 | 9 | 3.6 ± 0.7 | 21 | 1.5 ± 0.2 | 8 |
| 8 | 99.1 ± 0.1 | 635 | 0.6 ± 0.1 | 1 | 0.3 ± 0.0 | 2 | 0.1 ± 0.0 | 1 |
| Lung cancer cells | | | | | | | | |
| 0 | 9.4 ± 0.2 | 100 | 43.3 ± 0.3 | 100 | 7.1 ± 0.1 | 100 | 40.8 ± 0.1 | 100 |
| 1 | 46.5 ± 1.7 | 441 | 23.6 ± 0.4 | 54 | 11.8 ± 0.1 | 168 | 18.5 ± 1.2 | 45 |
| 3 | 61.8 ± 0.7 | 660 | 13.1 ± 1.4 | 30 | 9.8 ± 0.7 | 139 | 15.0 ± 0.7 | 36 |
| 5 | 96.6 ± 0.2 | 1030 | 2.3 ± 0.1 | 5 | 0.8 ± 0.0 | 11 | 0.4 ± 0.0 | 1 |
| 8 | 97.2 ± 0.6 | 1037 | 1.9 ± 0.4 | 4 | 0.4 ± 0.4 | 6 | 0.4 ± 0.5 | 1 |
| Breast cancer cells | | | | | | | | |
| 0 | 2.9 ± 0.6 | 100 | 66.8 ± 1.2 | 100 | 13.1 ± 0.6 | 100 | 18.2 ± 0.4 | 100 |
| 1 | 12.0 ± 0.8 | 441 | 71.2 ± 0.4 | 107 | 6.4 ± 0.6 | 49 | 10.7 ± 1.0 | 59 |
| 3 | 77.1 ± 0.4 | 2633 | 18.7 ± 1.0 | 27 | 2.4 ± 0.3 | 18 | 1.3 ± 0.2 | 7 |
| 5 | 92.0 ± 0.3 | 3141 | 6.8 ± 0.3 | 10 | 0.8 ± 0.0 | 6 | 0.4 ± 0.0 | 2 |
| 8 | 97.1 ± 0.4 | 3313 | 2.5 ± 0.3 | 4 | 0.2 ± 0.0 | 2 | 0.2 ± 0.1 | 1 |

Pharmacological Experiment 4.

Effect of the Water-soluble Extract Prepared from *Solanum incanum* L. According to this Invention on Cancer Cell Morphology To investigate the morphological changes of the cancer cells induced by the water-soluble extract prepared from *Solanum incanum* L. according to this invention, the morphologies of the cancer cells stained with hematoxylin were inspected using light-microscopy.

Methodologies:

First, a suitable amount of liver cancer cells, lung cancer cells, and breast cancer cells which were treated with the water-soluble extract (30 μg/ml) of *Solanum incanum* L. according to this invention for 1, 3, 5, and 8 hrs were centrifuged in Cytospin at 800 rpm for 10 min to obtain cytoslides. The cells were fixed in 4% of paraformaldehyde for 30 min and stained with hematoxylin, followed by removal of the excess dye by 70%, 80%, 90%, 95%, and 100% absolute alcohol. The cytoslides were placed in xylene for dehydration treatment and were covered by a cover slide and a mounting medium. The changes of cell morphology were observed using light microscope (Olympus CX-40) at 400× and recorded.

Figure 10:
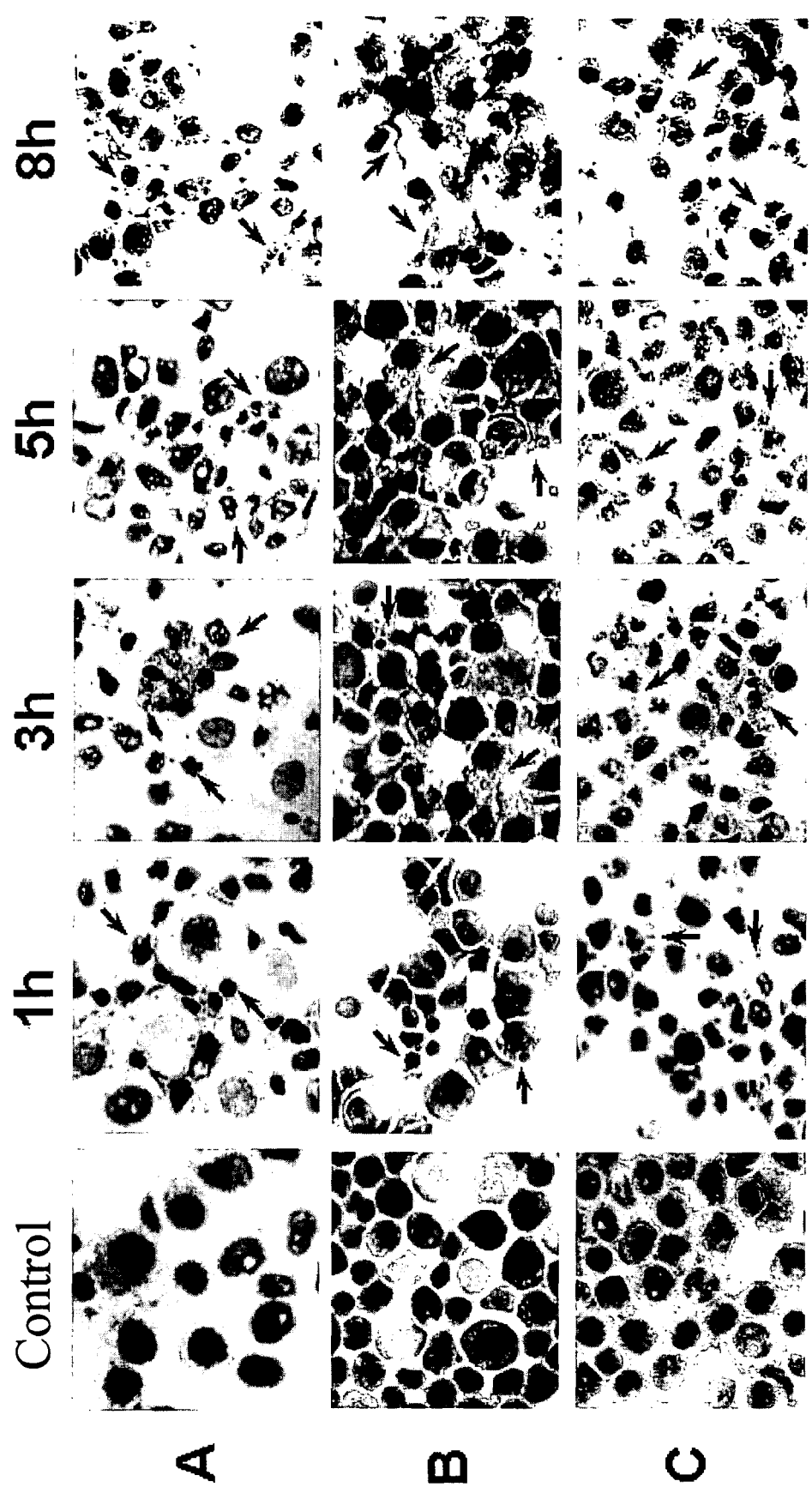
FIG. 10 is a set of photographs illustrating morphological changes of liver cancer cells (Line A), lung cancer cells (Line B), and breast cancer cells (Line C) treated with the water-soluble extract obtained from *Solanum incanum* L. according to the present invention.

Results:

FIG. 10 shows the morphological changes of human cancer cells before and after the cells were treated with the water-soluble extract (30 μg/ml) prepared from *Solanum incanum* L. according to this invention for 1, 3, 5, and 8 hrs, in which line A denotes Hep3B, line B denotes H441, and line C denotes MCF-7. The cells not treated with the extract were used as a control group, and the arrows indicated the typical morphological changes of cells.

As shown in FIG. 10, nucleuses reduction, chromatin condensation, and presence of apoptotic bodies were observed in the cancer cells after they were treated with the water-soluble extract prepared from *Solanum incanum* L. according to this invention for 1 hour. At the same time, the morphological changes of the cancer cells became more and more obvious with the progress of the reaction time until the cell membranes finally broke.

Since sub-G1 peak, chromatin condensation, and presence of apoptotic bodies are characteristics of apoptosis, the results shown in this assay and in pharmacological assay 3 clearly indicate that the water-soluble extract prepared from *Solanum incanum* L. according to this invention can initiate the mechanism of apoptosis in cancer cells to induce cell death.

Pharmacological Experiment 5.

Anti-cancer Effect of the Water-soluble Extract Prepared from *Solanum incanum* L. According to this Invention in vivo To confirm the anticancer effect of the water-soluble extract from *Solanum incanum* L. according to this invention in vivo, nude mice were used as the in vivo animal model.

Methodologies:

First, $2 \times 10^7$ H441 cells were implanted into the hind flank of the nude mice, BABL/c-nu-nu (8-week old, about 20–25 g) by subcutaneous injection. After the tumor was formed, it started to grow (about 10 days), the nude mice with tumor were randomly arranged in groups of 6–7 mice.

The nude mice in the injection group were administered intraperitoneally with 220 μg water-soluble extract dissolved in water using 0.8 mm needle once a day. Injection was continued for 3 days and discontinued for 4 days. The mice were weighed every two days and the tumor size was measured using a micrometer. The next treating course was proceeded, and observation continued for over two months. Tumor volume was calculated as a product of length×width× (height/2).

Each nude mouse in the oral-administration group mouse was orally administered with the water-soluble extract (600 μg) by a feeder once a day. Feeding was continued for 5 days and discontinued for 2 days. The weight of the nude mice and the tumor size were recorded in the above manner. Administration and observation were continued for over two months. Tumor volume was also calculated in the above manner.

Figure 11:
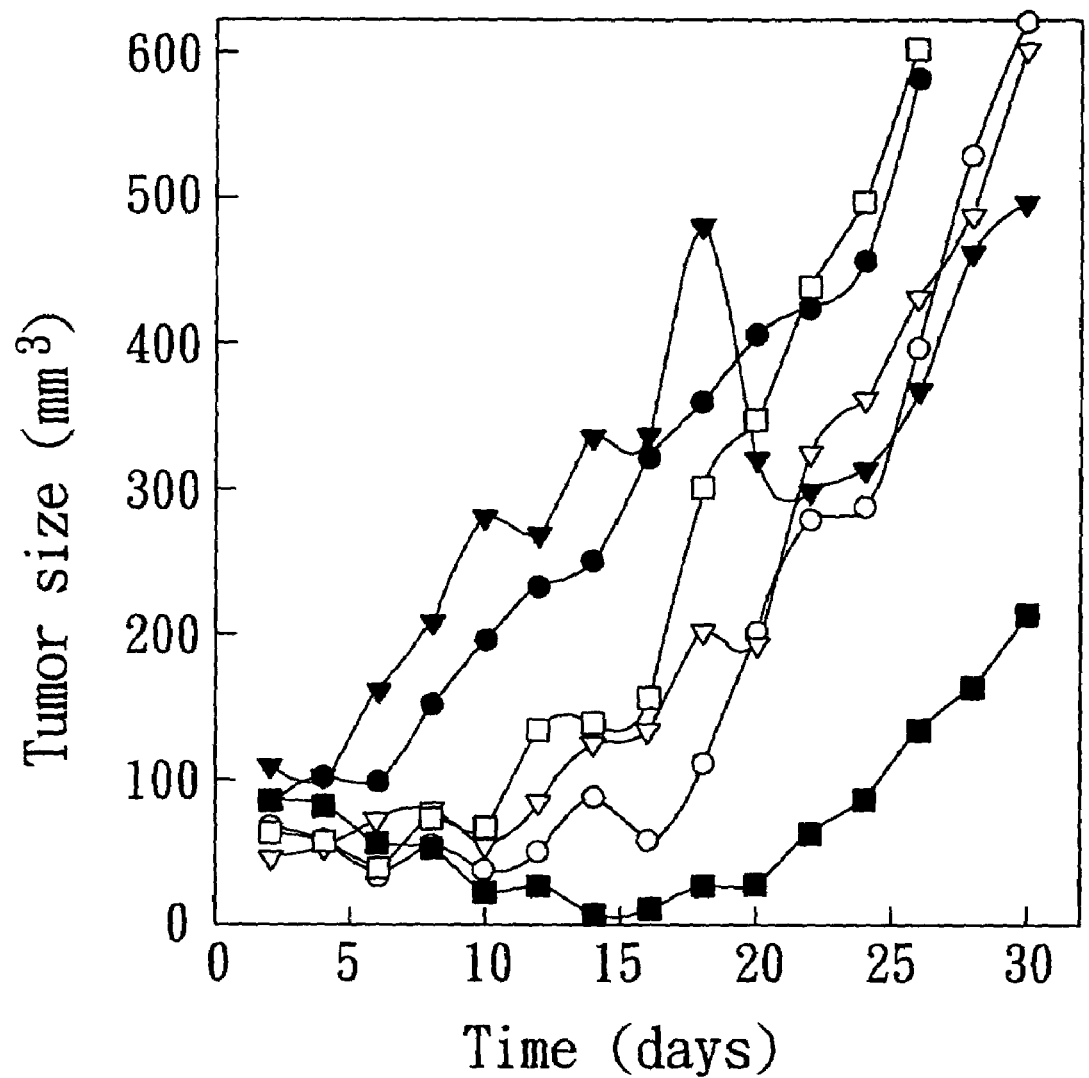
FIGS. 11A, 11B, and 11C are graphs showing changes in size of the tumors in nude mice that were not administered with the water-soluble extract obtained from *Solanum incanum* L. according to this invention, that were orally administered with the extract, and that were intraperitoneally administered with the extract, in which each curve represents the change in size of the tumor in one nude mouse.
Figure 11:
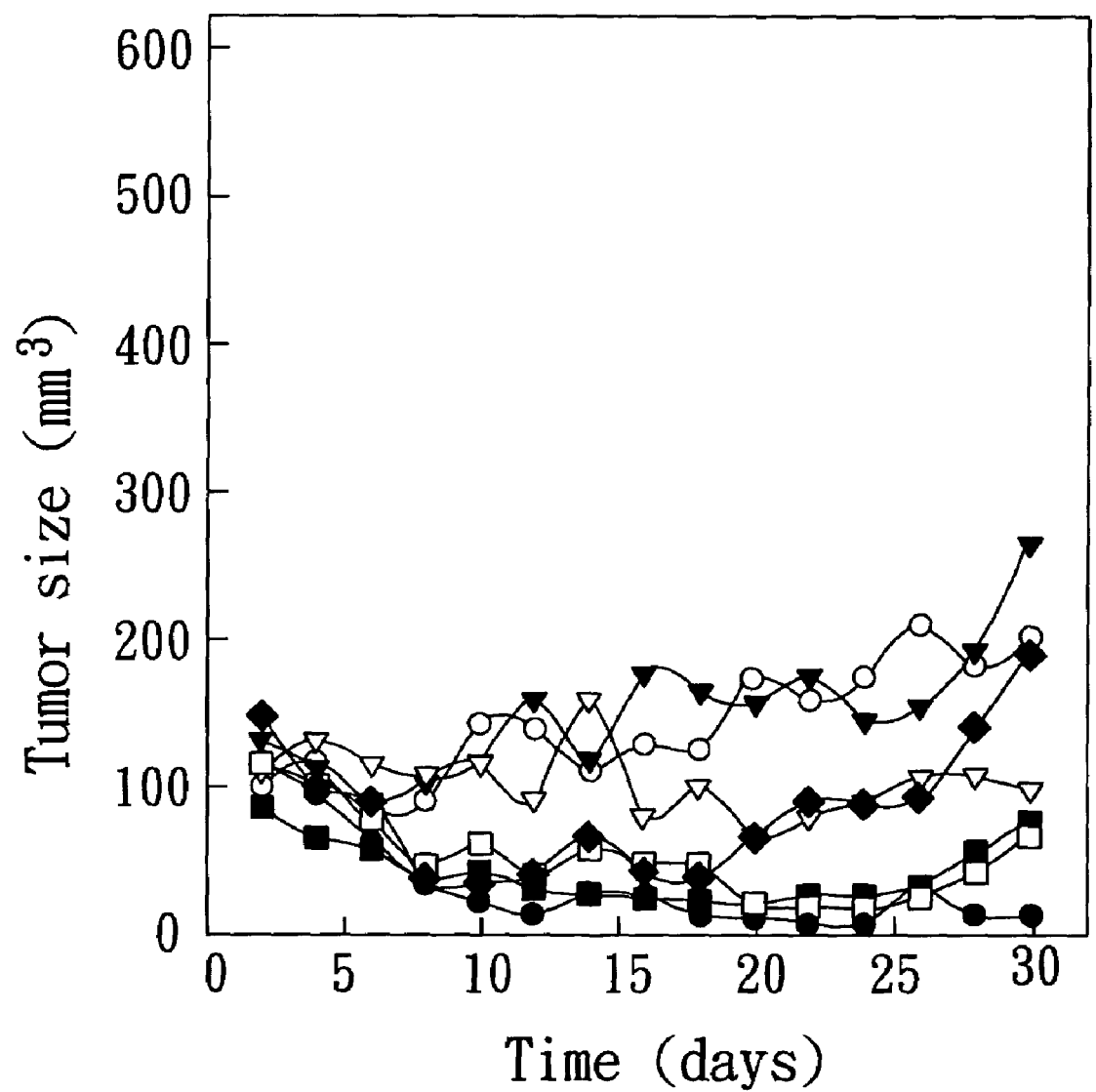
Figure 11:
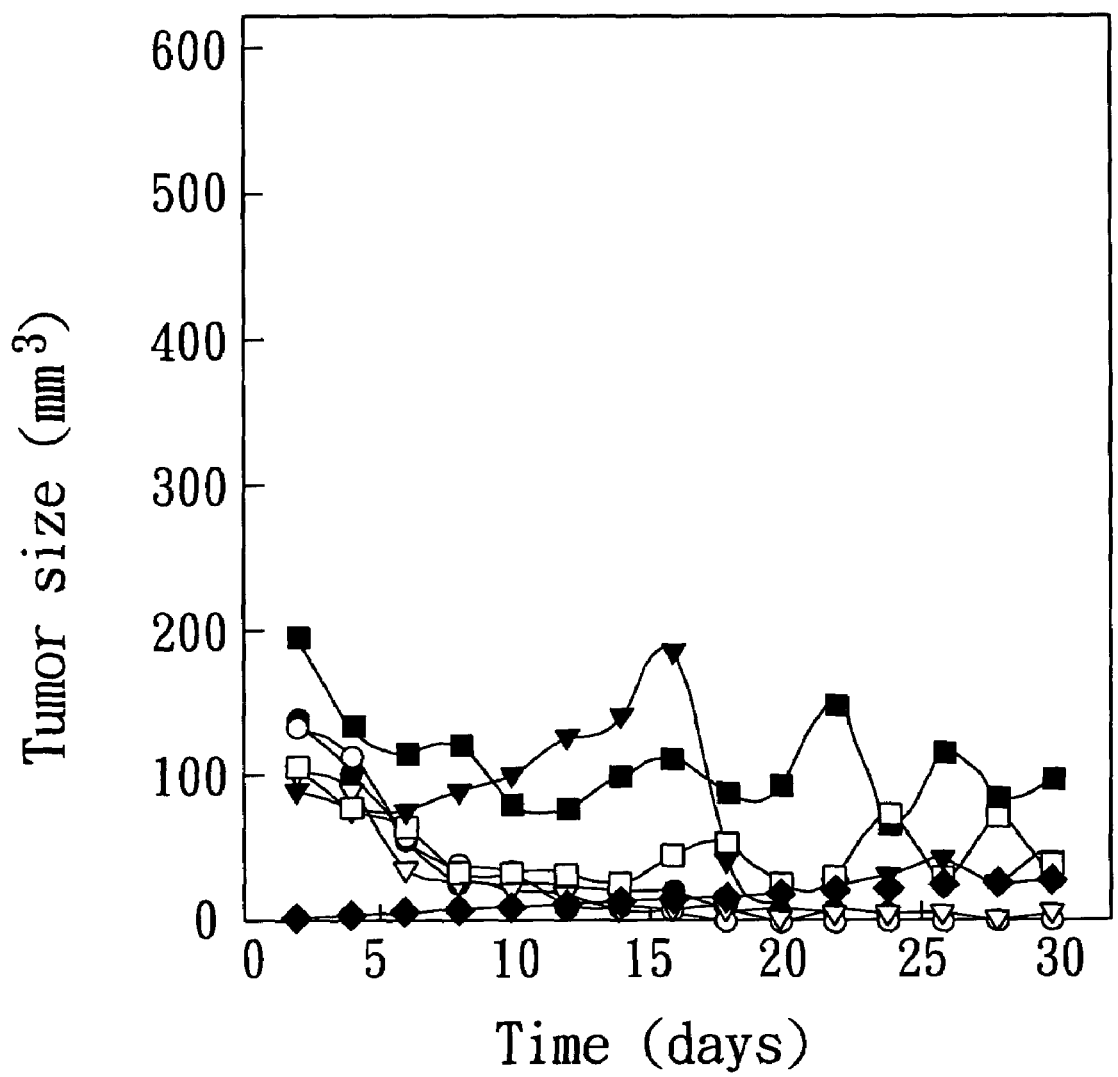

Results:

FIGS. 11A, 11B, and 11C respectively show the changes in tumor size in the nude mice, in which FIG. 11A showed the change in size of the tumor in the mice of the control group (6 nude mice) which were not administrated with the water-soluble extract obtained from *Solanum incanum* L. according to this invention; FIG. 11B showed the change in tumor size in the oral-administration group (7 nude mice); and FIG. 11C showed the change in tumor size in the injection group (7 nude mice).

As shown in FIGS. 11A, 11B, and 11C, the size of the tumor in the mice of the control group which were not administered with the water-soluble extract obtained from *Solanum incanum* L. according to this invention were found to increase rapidly, almost six times the original size after 1 month. However, the tumors in the nude mice orally administered with the water-soluble extract obtained from *Solanum incanum* L. according to this invention largely shrank or disappeared. Although the tumor in some slightly increased in size, the growth rate was far slower as compared with the control group. As for the nude mice intraperitoneally administered with the water-soluble extract obtained from *Solanum incanum* L. according to this invention, the tumors in all of the mice shrank or disappeared. The results show that oral or intraperitoneal administration of the water-soluble extract obtained from *Solanum incanum* L. according to this invention was effective in retarding the growth of the tumor implanted into nude mice, reducing the size thereof, and even eliminating the same, and that the effect was better in the intraperitoneal-administration group than in the oral-administration group.

Pharmacological Experiment 6.

Anti-cancer Effect of Solasonine and Solamargine Further Purified from the Water-soluble Extract of *Solanum incanum* L. According to this Invention in vivo The experiment was used to study the bioactivity of solasonine and solamargine purified from the water-soluble extract of *Solanum incanum* L. according to this invention using HPLC.

Methodologies:

According to HPLC procedure described in Example 2, the two compounds, solasonine and solamargine, which can likewise be directly dissolved in water, were further separated and purified from the water-soluble extract of *Solanum incanum* L. according to this invention.

Cytotoxicity was determined by MTS tetrazolium salt assay disclosed in Pharmacological assay 1. H441 cells were treated with various dosages of solasonine and solamargine purified from the water-soluble extract of *Solanum incanum* L. according to this invention for 12 hrs, followed by calorimetric determination of cell viability according to the manufacturer's procedure (CellTiter 96™ AQ, Promega, Madison, USA). Data were expressed as means ±SD from three experiments.

Figure 12:
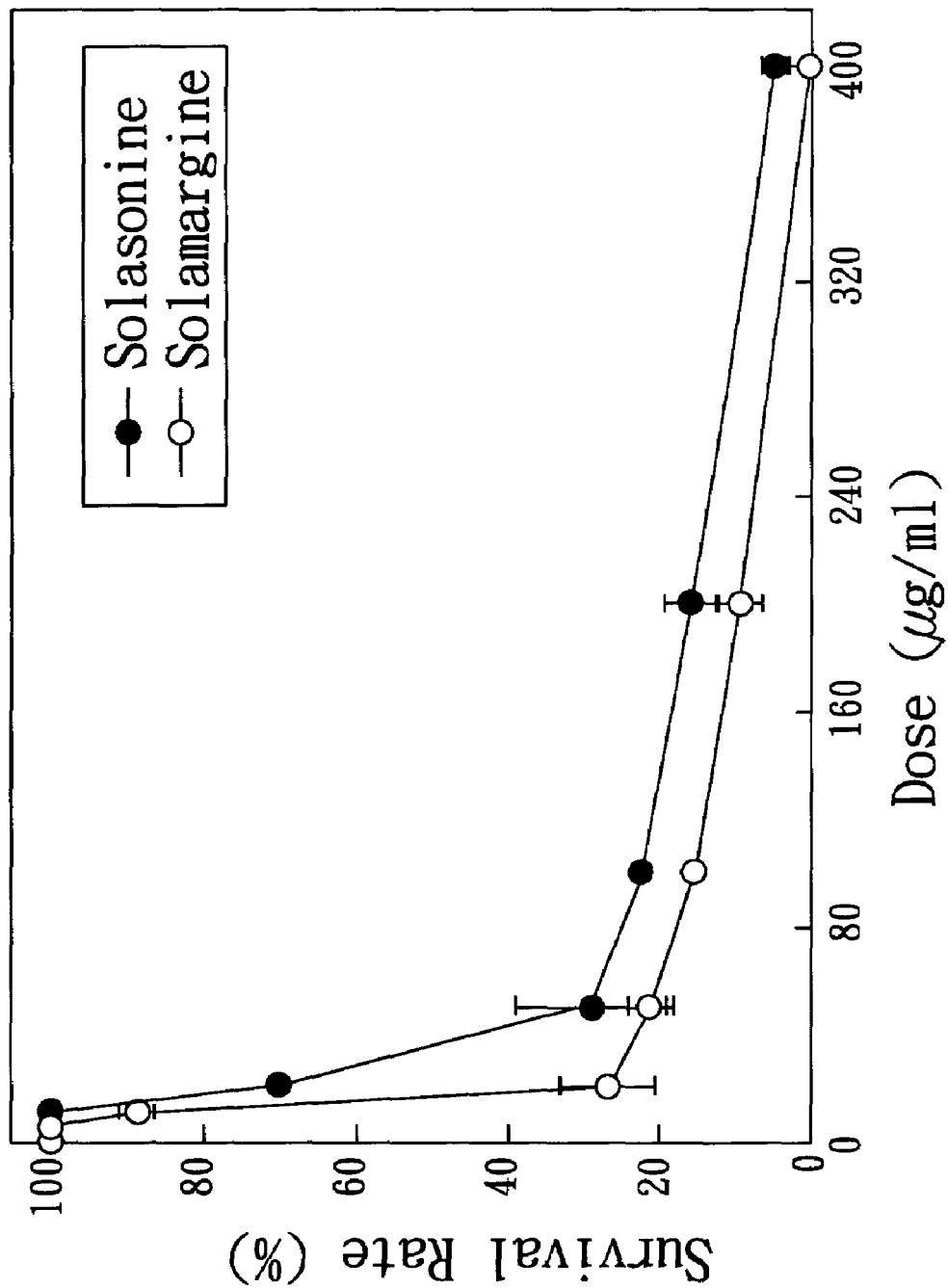
FIG. 12 is a graph showing the inhibitory effect of solasonine and solamargine obtained from *Solanum incanum* L. according to the present invention on the growth of human lung cancer cells.

Results:

FIG. 12 shows that the growth of human lung cancer cells can be effectively inhibited by solasonine and solamargine purified from the water-soluble extract of *Solanum incanum* L. according to this invention. As shown, solasonine and solamargine purified from the water-soluble extract of *Solanum incanum* L. according to this invention have remarkable anticancer activities.

In summary, the applicant successfully obtained a water-soluble extract from a plant of *Solanum* genus, established conditions for scientific analysis during extraction of the water-soluble extract, and obtained the active compounds thereof so that effective quality control is possible. In addition, the water-soluble extract according to this invention has been proven to possess the activities of inhibiting the growth of cancer cells and initiating the apoptotic mechanism of cancer cells. These facts indicate that the water-soluble extract of this invention has potentials in inhibiting the growth of cancer cells and detecting cancer cells.

All patents and literature references cited in the present specification are hereby incorporated by reference in their entirety. In case of conflict, the present description, including definitions, will prevail.

While the invention has been described with reference to the above specific embodiments, it is apparent that numerous modifications and variations can be made without departing from the scope and spirit of this invention. It is therefore intended that this invention be limited only as indicated by the appended claims.

The invention claimed is:

1. A water-soluble extract from a plant of *Solanum* genus, consisting essentially of at least 60%–90% of solamargine and solasonine.

2. The water-soluble extract according to claim 1, which is extracted from a plant of *Solanum* genus selected from the group consisting of:

*Solanum incanum* L., *Solanum indicum, Solanum nigrum, Solanum capsicastrum, Solanum xanthocarpum, Solanum melongena, Solanum coagulans, Solanum tunigrum, Solanum sodomeum, Solanum turburosum, Solanum aculeastrum, Solanum lycocarpum, Solanum khasianum, Solanum suaveolens, Solanum uporo, Solanum abutiloides, Solanum coccineum, Solanum unguiculatum, Solanum robustum, Solanum anguivi, Solanum platanifolium, Solanum mammosum,* and a combination thereof.

3. The water-soluble extract according to claim 2, which is extracted from *Solanum incanum* L.

4. The water-soluble extract according to claim 2, which is extracted from *Solanum nigrum*.

5. The water-soluble extract according to claim 1, which is prepared from a process comprising the steps of:

(a) subjecting a plant material of a plant of *Solanum* genus to an extraction treatment using an acidic aqueous solution with a pH value of 3~5, such that an aqueous solution is obtained;

(b) adjusting the pH value of the aqueous solution obtained in step (a) to pH 8~10 with a base, such that a precipitate is formed;

(c) washing the precipitate formed in step (b) with water, followed by drying, such that a dried product is obtained;

(d) admixing the dried product obtained in step (c) with chloroform, followed by addition of a suitable amount of a 100% alcohol, such that a chloroform-alcohol mixture is formed;

(e) mixing the chloroform-alcohol mixture formed in step (d) with a water/alcohol solution having a predetermined water:alcohol ratio, such that a mixture containing a chloroform-based layer and a non-chloroform-based layer is obtained;

(f) removing the chloroform-based layer from the mixture obtained in step (e), followed by addition of a suitable amount of water; and (g) obtaining a supernatant from the resultant mixture of step (f), followed by drying the supernatant, wherein the resultant dried product is able to be directly dissolved in water to form a yellowish clear and transparent aqueous solution.

6. The water-soluble extract according to claim 5, wherein in step (a) of said process, the used plant material is at least one of the fruit, root, stem, and leaf of said plant of *Solanum* genus.

7. The water-soluble extract according to claim 6, wherein in step (a) of said process, the used plant material is the fruit of said plant of *Solanum* genus.

8. The water-soluble extract according to claim 6, wherein in step (a) of said process, the plant material is the whole plant of said plant of *Solanum* genus.

9. The water-soluble extract according to claim 5, wherein in step (a) of said process, the plant material of said plant of *Solanum* genus has been chopped in a preliminary treatment.

10. The water-soluble extract according to claim 5, wherein in step (a) of said process, the aqueous solution is obtained by conducting centrifugation subsequent to the extraction treatment.

11. The water-soluble extract according to claim 5, wherein in step (a) of said process, the acidic aqueous solution in the extraction treatment is an aqueous solution containing formic acid, acetic acid, or hydrochloric acid.

12. The water-soluble extract according to claim 5, wherein in step (b) of said process, the base is an alkaline aqueous solution containing a compound selected from the group consisting of alkali hydroxides and ammonium hydroxide.

13. The water-soluble extract according to claim 12, wherein in step (b) of said process, the base is an alkaline aqueous solution containing ammonium hydroxide.

14. The water-soluble extract according to claim 12, wherein in step (b) of said process, the base is an alkaline aqueous solution containing sodium hydroxide.

15. The water-soluble extract according to claim 5, wherein in step (b) of said process, the precipitate is obtained by conducting centrifugation subsequent to the pH value adjustment.

16. The water-soluble extract according to claim 5, wherein in step (c) of said process, the drying treatment is selected from the group consisting of lyophilization, spray-drying, evaporation, heat-drying, and a combination thereof.

17. The water-soluble extract according to claim 5, wherein, in step (c) of said process, the dried product is obtained by washing the precipitate formed in step (b) with water and suspending the washed precipitate in water, followed by lyophilization.

18. The water-soluble extract according to claim 5, wherein in steps (d) and (e) of said process, the alcohol is selected from the group consisting of methanol, ethanol, propyl alcohol, and a combination thereof.

19. The water-soluble extract according to claim 5, wherein in step (f) of said process, the removal of the chloroform-based layer is conducted by centrifugation.

20. The water-soluble extract according to claim 5, wherein in step (g) of said process, the drying treatment is selected from the group consisting of lyophilization, spray-drying, evaporation, heat-drying, and a combination thereof.

21. The water-soluble extract according to claim 1, which is in a form of water-soluble particles with a nanoparticle size.

22. The water-soluble extract according to claim 20, which is in a form of water-soluble particles with a particle size less than 1 μm.

23. The water-soluble extract according to claim 1, which is composed of more than 75% of solasonine and solamargine.

24. The water-soluble extract according to claim 1, which has a solasonine to solamargine ratio ranging from 0.3:1.0 to 1.0:0.6.

25. The water-soluble extract according to claim 1, which has a solasonine to solamargine ratio ranging from 0.4:1.0 to 0.9:1.0.

26. The water-soluble extract according to claim 1, which has a solasonine to solamargine ratio around 0.7:1.0.

27. The water-soluble extract according to claim 1, which has a water solubility ranging from 2 to 20 mg/ml or higher.

28. The water-soluble extract according to any one of claims 1–27, which can be used in manufacture of a medicament effective in inhibiting the growth of tumor/cancer cells.

29. A pharmaceutical composition, comprising a water-soluble extract according to any one of claims 1–27 and, optionally, a pharmaceutically acceptable carrier.

30. A pharmaceutical composition for inhibiting the growth of tumor/cancer cells, comprising a water-soluble extract according to any one of claims 1–27 and, optionally, a pharmaceutically acceptable carrier.

31. A process for preparing a water-soluble extract from a plant of *Solanum* genus, comprising the steps of:
(a) subjecting a plant material of a plant of *Solanum* genus to an extraction treatment using an acidic aqueous solution with a pH value of 3~5, such that an aqueous solution is obtained;
(b) adjusting the pH value of the aqueous solution obtained in step (a) to pH 8~10 with a base, such that a precipitate is formed;
(c) washing the precipitate formed in step (b) with water, followed by drying, such that a dried product is obtained;
(d) admixing the dried product obtained in step (c) with chloroform, followed by addition of a suitable amount of a 100% alcohol, such that a chloroform-alcohol mixture is formed;
(e) mixing the chloroform-alcohol mixture formed in step (d) with a water/alcohol solution having a predetermined water:alcohol ratio, such that a mixture containing a chloroform-based layer and a non-chloroform-based layer is obtained;
(f) removing the chloroform-based layer from the mixture obtained in step (e), followed by addition of a suitable amount of water; and
(g) obtaining a supernatant from the resultant mixture of step (f), followed by drying the supernatant, wherein the resultant dried product is able to be directly dissolved in water to form a yellowish clear and transparent aqueous solution.

32. The process according to claim 31, wherein in step (a), the plant material of said plant of *Solanum* genus has been chopped in a preliminary treatment.

33. The process according to claim 31, wherein in step (a), the plant material is at least one of the fruit, root, stem, and leaf of said plant of *Solanum* genus.

34. The process according to claim 31, wherein in step (a), the plant material is the fruit of said plant of *Solanum* genus.

35. The process according to claim 31, wherein in step (a), the plant material is the whole plant of said plant of *Solanum* genus.

36. The process according to claim 31, wherein in step (a), the plant material is from a plant of *Solanum* genus selected from the group consisting of *Solanum incanum* L., *Solanum indicum, Solanum nigrum, Solanum capsicastrum, Solanum xanthocarpum, Solanum melongena, Solanum coagulans, Solanum tunigrum, Solanum sodomeum, Solanum turburosum, Solanum aculeastrum, Solanum lycocarpum, Solanum khasianum, Solanum suaveolens, Solanum uporo, Solanum abutiloides, Solanum coccineum, Solanum unguiculatum, Solanum robustum, Solanum anguivi, Solanum platanifolium, Solanum mammosum*, and a combination thereof.

37. The process according to claim 36, wherein in step (a), the plant material is from *Solanum incanum* L.

38. The process according to claim 36, wherein in step (a), the plant material is from *Solanum nigrum*.

39. The process according to claim 31, wherein in step (a), the aqueous solution is obtained by conducting centrifugation subsequent to the extraction treatment.

40. The process according to claim 31, wherein in step (a), the acidic aqueous solution in the extraction treatment is an aqueous solution containing formic acid, acetic acid, or hydrochloric acid.

41. The process according to claim 31, wherein in step (b), the base is an alkaline aqueous solution containing a compound selected from the group consisting of alkali hydroxides and ammonium hydroxide.

42. The process according to claim 41, wherein in step (b), the base is an alkaline aqueous solution containing ammonium hydroxide.

43. The process according to claim 41, wherein in step (b), the base is an alkaline aqueous solution containing sodium hydroxide.

44. The process according to claim 31, wherein in step (b), the precipitate is obtained by conducting centrifugation subsequent to the pH value adjustment.

45. The process according to claim 31, wherein in step (c), the drying treatment is selected from the group consisting of lyophilization, spray-drying, evaporation, heat-drying, and a combination thereof.

46. The process according to claim 31, wherein in step (c), the dried product is obtained by washing the precipitate formed in step (b) with water and suspending the washed precipitate in water, followed by lyophilization.

47. The process according to claim 31, wherein in steps (d) and (e), the alcohol is selected from the group consisting of methanol, ethanol, propyl alcohol, and a combination thereof.

48. The process according to claim 31, wherein, in step (f), the removal of the chloroform-based layer is conducted by centrifugation.

49. The process according to claim 31, wherein in step (g), the drying treatment is selected from the group consisting of: lyophilization, spray-drying, evaporation, heat-drying, and a combination thereof.

50. The process according to claim 31, wherein the resultant product from step (g) is in a form of water-soluble particles with a nanoparticle size.

51. The process according to claim 50, wherein the resultant product from step (g) is in a form of water-soluble particles with a particle size less than 1 μm.

52. The process according to claim 31, wherein the resultant product from step (g) consists essentially of at least 60%–90% of solasonine and solamargine.

53. The process according to claim 52, wherein the resultant product from step (g) is composed of more than 75% of solasonine and solamargine.

54. The process according to claim 31, wherein the resultant product from step (g) has a solasonine to solamargine ratio ranging from 0.3:1.0 to 1.0:0.6.

55. The process according to claim 31, wherein the resultant product from step (g) has a solasonine to solamargine ratio ranging from 0.4:1.0 to 0.9:1.0.

56. The process according to claim 31, wherein the resultant product from step (g) has a solasonine to solamargine ratio around 0.7:1.0.

57. The process according to claim 31, wherein the resultant product from step (g) has a water solubility ranging from 2 to 20 mg/ml or higher.

58. A pharmaceutical composition comprising a water-soluble extract prepared by a process according to any one of claims 31–57 and, optionally, a pharmaceutically acceptable carrier.

59. A pharmaceutical composition for inhibiting the growth of tumor/cancer cells, comprising a water-soluble extract prepared by a process according to any one of claims 31–57 and, optionally, a pharmaceutically acceptable carrier.

* * * * *

UNITED STATES PATENT AND TRADEMARK OFFICE
CERTIFICATE OF CORRECTION

PATENT NO. : 7,078,063 B2 Page 1 of 1
APPLICATION NO. : 10/650942
DATED : July 18, 2006
INVENTOR(S) : Kuo It is certified that error appears in the above-identified patent and that said Letters Patent is hereby corrected as shown below:

On Title Page, Item (73), should read,
    Assignees: Kou-Wha Kuo, Kaohsiung (TW); and
    G & E Herbal Biotechnology Co., Ltd., Tainan (TW)

Signed and Sealed this

Twenty-fourth Day of October, 2006

JON W. DUDAS
*Director of the United States Patent and Trademark Office*